United States Patent
Cánovas Vidal et al.

(10) Patent No.: US 11,497,599 B2
(45) Date of Patent: Nov. 15, 2022

(54) DIFFRACTIVE INTRAOCULAR LENSES FOR EXTENDED RANGE OF VISION

(71) Applicant: AMO Groningen B.V., Groningen (NL)

(72) Inventors: Carmen Cánovas Vidal, Groningen (NL); Hendrik A. Weeber, Groningen (NL); Patricia Ann Piers, Groningen (NL)

(73) Assignee: AMO Groningen B.V., Groningen (NL)

( * ) Notice: Subject to any disclaimer, the term of this patent is extended or adjusted under 35 U.S.C. 154(b) by 470 days.

(21) Appl. No.: 15/923,911

(22) Filed: Mar. 16, 2018

(65) Prior Publication Data

US 2018/0263760 A1 Sep. 20, 2018

Related U.S. Application Data

(60) Provisional application No. 62/473,200, filed on Mar. 17, 2017.

(51) Int. Cl.
*A61F 2/16* (2006.01)
*G02C 7/04* (2006.01)
*A61F 2/14* (2006.01)

(52) U.S. Cl.
CPC ............ *A61F 2/1629* (2013.01); *A61F 2/164* (2015.04); *A61F 2/1618* (2013.01);
(Continued)

(58) Field of Classification Search
CPC ...... A61F 2/1629; A61F 2/164; A61F 2/1645; A61F 2/1654
See application file for complete search history.

(56) References Cited

U.S. PATENT DOCUMENTS 3,367,734 A   2/1968 Karl et al.
3,722,986 A   3/1973 Tagnon
(Continued)

FOREIGN PATENT DOCUMENTS

AU   2005230194 B2   12/2010
CA   2501217 A1   4/2004
(Continued)

OTHER PUBLICATIONS

Schwiegerling et al., "Representation of videokeratoscopic height data with Zernike polynomials," Journal of the Optical Society of America, 1995, 12 (10), 2105-2113.
(Continued)

*Primary Examiner* — Javier G Blanco
(74) *Attorney, Agent, or Firm* — Johnson & Johnson Surgical Vision, Inc.

(57) ABSTRACT

Apparatuses, systems and methods for providing improved ophthalmic lenses, particularly intraocular lenses (IOLs). Exemplary diffractive intraocular implants (IOLs) can include a diffractive profile having multiple diffractive zones. The diffractive zones can include a central zone that includes one or more echelettes and a peripheral zone beyond the central zone having one or more peripheral echelettes. The central diffractive zone can work in a higher diffractive order than a remainder of the diffractive profile. The combination of the central and peripheral zones and an optional intermediate zone provides a longer depth of focus than a diffractive profile defined just by a peripheral and/or optional intermediate zone.

33 Claims, 7 Drawing Sheets

(52) U.S. Cl.
CPC .......... *A61F 2/1645* (2015.04); *A61F 2/1654* (2013.01); *A61F 2/1656* (2013.01); *G02C 7/042* (2013.01); *G02C 7/044* (2013.01); *A61F 2/1451* (2015.04); *A61F 2/1602* (2013.01); *A61F 2240/001* (2013.01); *G02C 2202/20* (2013.01)

(56) References Cited

U.S. PATENT DOCUMENTS

| | | |
|---|---|---|
| 4,210,391 A | 7/1980 | Cohen et al. |
| 4,338,005 A | 7/1982 | Cohen |
| 4,340,283 A | 7/1982 | Cohen et al. |
| 4,460,275 A | 7/1984 | Spriggs |
| 4,504,892 A | 3/1985 | Zulfilar |
| 4,504,982 A | 3/1985 | Burk |
| 4,580,883 A | 4/1986 | Shinohara |
| 4,606,626 A | 8/1986 | Shinohara |
| 4,637,697 A | 1/1987 | Freeman |
| 4,640,593 A | 2/1987 | Shinohara |
| 4,641,934 A | 2/1987 | Freeman |
| 4,642,112 A | 2/1987 | Freeman |
| 4,655,565 A | 4/1987 | Freeman |
| 4,710,193 A | 12/1987 | Volk |
| 4,762,408 A | 8/1988 | Shinohara |
| 4,778,462 A | 10/1988 | Grendahl |
| 4,795,462 A | 1/1989 | Grendahl |
| 4,798,608 A | 1/1989 | Grendahl |
| 4,798,609 A | 1/1989 | Grendahl |
| 4,856,234 A | 8/1989 | Goins |
| 4,856,889 A | 8/1989 | Guilino et al. |
| 4,881,804 A | 11/1989 | Cohen |
| 4,881,805 A | 11/1989 | Cohen |
| 4,898,461 A | 2/1990 | Portney |
| 4,932,970 A | 6/1990 | Portney |
| 4,936,666 A | 6/1990 | Futhey |
| 4,957,506 A | 9/1990 | Mercier |
| 4,978,211 A | 12/1990 | Cornu et al. |
| 4,995,714 A | 2/1991 | Cohen |
| 4,995,715 A | 2/1991 | Cohen |
| 5,016,977 A | 5/1991 | Baude et al. |
| 5,017,000 A | 5/1991 | Cohen |
| 5,019,098 A | 5/1991 | Mercier |
| 5,050,981 A | 9/1991 | Roffman |
| 5,054,905 A | 10/1991 | Cohen |
| 5,056,908 A | 10/1991 | Cohen |
| 5,061,058 A | 10/1991 | Guilino et al. |
| 5,066,301 A | 11/1991 | Wiley |
| 5,076,684 A | 12/1991 | Simpson et al. |
| 5,089,023 A | 2/1992 | Swanson |
| 5,089,024 A | 2/1992 | Christie et al. |
| 5,096,285 A | 3/1992 | Silberman |
| 5,100,226 A | 3/1992 | Freeman |
| 5,104,212 A | 4/1992 | Taboury et al. |
| 5,112,351 A | 5/1992 | Christie et al. |
| 5,114,220 A | 5/1992 | Baude et al. |
| 5,116,111 A | 5/1992 | Simpson et al. |
| 5,117,306 A | 5/1992 | Cohen |
| 5,120,120 A | 6/1992 | Cohen |
| 5,121,979 A | 6/1992 | Cohen |
| 5,121,980 A | 6/1992 | Cohen |
| 5,129,718 A | 7/1992 | Futhey et al. |
| 5,144,483 A | 9/1992 | Cohen |
| 5,148,205 A | 9/1992 | Guilino et al. |
| 5,161,057 A | 11/1992 | Johnson |
| 5,173,723 A | 12/1992 | Volk et al. |
| 5,178,636 A | 1/1993 | Silberman |
| 5,191,366 A | 3/1993 | Kashiwagi |
| 5,220,359 A | 6/1993 | Roffman |
| 5,225,858 A | 7/1993 | Portney |
| 5,229,797 A | 7/1993 | Futhey et al. |
| 5,236,970 A | 8/1993 | Christ et al. |
| 5,257,132 A | 10/1993 | Ceglio et al. |
| 5,260,727 A | 11/1993 | Oksman et al. |
| 5,322,649 A | 6/1994 | Rheinish et al. |
| 5,344,447 A | 9/1994 | Swanson |
| 5,349,394 A | 9/1994 | Freeman et al. |
| 5,349,471 A | 9/1994 | Morris et al. |
| 5,381,190 A | 1/1995 | Rehse et al. |
| 5,384,606 A | 1/1995 | Koch et al. |
| 5,408,281 A | 4/1995 | Zhang |
| 5,443,506 A | 8/1995 | Garabet |
| 5,443,507 A | 8/1995 | Jacobi |
| 5,444,106 A | 8/1995 | Zhou et al. |
| 5,446,508 A | 8/1995 | Kitchen |
| 5,448,312 A | 9/1995 | Roffman et al. |
| 5,485,228 A | 1/1996 | Roffman et al. |
| 5,581,405 A | 12/1996 | Meyers et al. |
| 5,589,982 A | 12/1996 | Faklis et al. |
| 5,629,800 A | 5/1997 | Hamblen |
| 5,652,638 A | 7/1997 | Roffman et al. |
| 5,674,284 A | 10/1997 | Chang et al. |
| 5,682,223 A | 10/1997 | Menezes et al. |
| 5,683,457 A | 11/1997 | Gupta et al. |
| 5,684,560 A | 11/1997 | Roffman et al. |
| 5,684,595 A | 11/1997 | Kato et al. |
| 5,699,142 A | 12/1997 | Lee et al. |
| 5,715,031 A | 2/1998 | Roffman et al. |
| 5,715,091 A | 2/1998 | Meyers |
| 5,724,258 A | 3/1998 | Roffman |
| 5,728,156 A | 3/1998 | Gupta et al. |
| 5,748,282 A | 5/1998 | Freeman |
| 5,760,871 A | 6/1998 | Kosoburd et al. |
| 5,777,719 A | 7/1998 | Williams et al. |
| 5,796,462 A | 8/1998 | Roffman et al. |
| 5,800,532 A | 9/1998 | Lieberman |
| 5,805,260 A | 9/1998 | Roffman et al. |
| 5,822,091 A | 10/1998 | Baker |
| 5,838,496 A | 11/1998 | Maruyama et al. |
| 5,847,802 A | 12/1998 | Menezes et al. |
| 5,888,122 A | 3/1999 | Gupta et al. |
| 5,895,422 A | 4/1999 | Hauber |
| 5,895,610 A | 4/1999 | Chang et al. |
| 5,929,969 A | 7/1999 | Roffman |
| 5,968,094 A | 10/1999 | Werblin et al. |
| 5,968,095 A | 10/1999 | Norrby |
| 5,982,543 A | 11/1999 | Fiala |
| 6,007,747 A | 12/1999 | Blake et al. |
| 6,019,472 A | 2/2000 | Koester et al. |
| 6,050,687 A | 4/2000 | Bille et al. |
| 6,070,980 A | 6/2000 | Obara et al. |
| 6,082,856 A | 7/2000 | Dunn et al. |
| 6,086,204 A | 7/2000 | Magnante |
| 6,089,711 A | 7/2000 | Blankenbecler et al. |
| 6,095,651 A | 8/2000 | Williams et al. |
| 6,120,148 A | 9/2000 | Fiala et al. |
| 6,126,283 A | 10/2000 | Wen et al. |
| 6,126,286 A | 10/2000 | Portney |
| 6,139,145 A | 10/2000 | Israel |
| 6,142,625 A | 11/2000 | Sawano et al. |
| 6,145,987 A | 11/2000 | Baude et al. |
| 6,154,323 A | 11/2000 | Kamo |
| 6,199,986 B1 | 3/2001 | Williams et al. |
| 6,210,005 B1 | 4/2001 | Portney |
| 6,215,096 B1 | 4/2001 | Von Wallfeld et al. |
| 6,224,211 B1 | 5/2001 | Gordon |
| 6,231,603 B1 | 5/2001 | Lang, I et al. |
| 6,270,220 B1 | 8/2001 | Keren |
| 6,271,915 B1 | 8/2001 | Frey et al. |
| 6,325,510 B1 | 12/2001 | Golub et al. |
| 6,338,559 B1 | 1/2002 | Williams et al. |
| 6,353,503 B1 | 3/2002 | Spitzer et al. |
| 6,413,276 B1 | 7/2002 | Werblin |
| 6,429,972 B1 | 8/2002 | Ota et al. |
| 6,439,720 B1 | 8/2002 | Graves et al. |
| 6,457,826 B1 | 10/2002 | Lett |
| 6,462,874 B1 | 10/2002 | Soskind |
| 6,464,355 B1 | 10/2002 | Gil |
| 6,474,814 B1 | 11/2002 | Griffin |
| 6,488,708 B2 | 12/2002 | Sarfarazi |
| 6,491,721 B2 | 12/2002 | Freeman et al. |
| 6,497,483 B2 | 12/2002 | Frey et al. |
| 6,511,180 B2 | 1/2003 | Guirao et al. |
| 6,520,638 B1 | 2/2003 | Roffman et al. |
| 6,527,389 B2 | 3/2003 | Portney |

(56) References Cited

U.S. PATENT DOCUMENTS

| | | |
|---|---|---|
| 6,533,416 B1 | 3/2003 | Fermigier et al. |
| 6,536,899 B1 | 3/2003 | Fiala |
| 6,537,317 B1 | 3/2003 | Steinert et al. |
| 6,547,391 B2 | 4/2003 | Ross, III et al. |
| 6,547,822 B1 | 4/2003 | Lang |
| 6,554,425 B1 | 4/2003 | Roffman et al. |
| 6,554,859 B1 | 4/2003 | Lang et al. |
| 6,557,992 B1 | 5/2003 | Dwyer et al. |
| 6,576,012 B2 | 6/2003 | Lang |
| 6,582,076 B1 | 6/2003 | Roffman et al. |
| 6,585,375 B2 | 7/2003 | Donitzky et al. |
| 6,609,673 B1 | 8/2003 | Johnson |
| 6,609,793 B2 | 8/2003 | Norrby et al. |
| 6,616,275 B1 | 9/2003 | Dick et al. |
| 6,655,802 B2 | 12/2003 | Zimmermann et al. |
| 6,685,315 B1 | 2/2004 | De |
| 6,705,729 B2 | 3/2004 | Piers et al. |
| 6,709,103 B1 | 3/2004 | Roffman et al. |
| 6,755,524 B2 | 6/2004 | Rubinstein et al. |
| 6,791,754 B2 | 9/2004 | Ogawa |
| 6,802,605 B2 | 10/2004 | Cox et al. |
| 6,808,262 B2 | 10/2004 | Chapoy et al. |
| 6,818,158 B2 | 11/2004 | Pham et al. |
| 6,827,444 B2 | 12/2004 | Williams et al. |
| 6,830,332 B2 | 12/2004 | Piers et al. |
| 6,835,204 B1 | 12/2004 | Stork et al. |
| 6,846,326 B2 | 1/2005 | Zadno-Azizi et al. |
| 6,848,790 B1 | 2/2005 | Dick et al. |
| 6,851,803 B2 | 2/2005 | Wooley et al. |
| 6,884,261 B2 | 4/2005 | Zadno-Azizi et al. |
| 6,923,539 B2 | 8/2005 | Simpson et al. |
| 6,923,540 B2 | 8/2005 | Ye et al. |
| 6,951,391 B2 | 10/2005 | Morris et al. |
| 6,957,891 B2 | 10/2005 | Fiala |
| 6,972,032 B2 | 12/2005 | Aharoni et al. |
| 6,986,578 B2 | 1/2006 | Jones |
| 7,025,456 B2 | 4/2006 | Morris et al. |
| 7,036,931 B2 | 5/2006 | Lindacher et al. |
| 7,048,759 B2 | 5/2006 | Bogaert et al. |
| 7,048,760 B2 | 5/2006 | Cumming |
| 7,061,693 B2 | 6/2006 | Zalevsky |
| 7,073,906 B1 | 7/2006 | Portney |
| 7,093,938 B2 | 8/2006 | Morris et al. |
| 7,111,938 B2 | 9/2006 | Andino et al. |
| 7,137,702 B2 | 11/2006 | Piers et al. |
| 7,156,516 B2 | 1/2007 | Morris et al. |
| 7,159,983 B2 | 1/2007 | Menezes et al. |
| 7,188,949 B2 | 3/2007 | Bandhauer et al. |
| 7,198,640 B2 | 4/2007 | Nguyen |
| 7,217,375 B2 | 5/2007 | Lai |
| 7,221,513 B2 | 5/2007 | Cho et al. |
| 7,232,218 B2 | 6/2007 | Morris et al. |
| 7,287,852 B2 | 10/2007 | Fiala |
| 7,293,873 B2 | 11/2007 | Dai et al. |
| 7,365,917 B2 | 4/2008 | Zalevsky |
| 7,377,640 B2 | 5/2008 | Piers et al. |
| 7,377,641 B2 | 5/2008 | Piers et al. |
| 7,441,894 B2 | 10/2008 | Zhang et al. |
| 7,455,404 B2 | 11/2008 | Bandhauer et al. |
| 7,475,986 B2 | 1/2009 | Dai et al. |
| 7,481,532 B2 | 1/2009 | Hong et al. |
| 7,543,937 B2 | 6/2009 | Piers et al. |
| 7,572,007 B2 | 8/2009 | Simpson |
| 7,604,350 B2 | 10/2009 | Dursteler et al. |
| 7,615,073 B2 | 11/2009 | Deacon et al. |
| 7,654,667 B2 | 2/2010 | Blum et al. |
| 7,670,371 B2 | 3/2010 | Piers et al. |
| 7,677,725 B2 | 3/2010 | Piers et al. |
| 7,717,558 B2 | 5/2010 | Hong et al. |
| 7,753,521 B2 | 7/2010 | Wooley et al. |
| 7,871,162 B2 | 1/2011 | Weeber |
| 7,883,207 B2 | 2/2011 | Iyer et al. |
| 7,896,916 B2 | 3/2011 | Piers et al. |
| 7,922,326 B2 | 4/2011 | Bandhauer et al. |
| 7,984,990 B2 | 7/2011 | Bandhauer et al. |
| 7,998,198 B2 | 8/2011 | Angelopoulos et al. |
| 8,128,222 B2 | 3/2012 | Portney |
| 8,157,374 B2 | 4/2012 | Bandhauer et al. |
| 8,192,022 B2 | 6/2012 | Zalevsky |
| 8,197,063 B2 | 6/2012 | Iyer et al. |
| 8,216,307 B2 | 7/2012 | Schaper, Jr. |
| 8,231,219 B2 | 7/2012 | Weeber |
| 8,231,673 B2 | 7/2012 | Sacharoff et al. |
| 8,235,525 B2 | 8/2012 | Lesage et al. |
| 8,240,850 B2 | 8/2012 | Apter et al. |
| 8,262,728 B2 | 9/2012 | Zhang et al. |
| 8,292,953 B2 | 10/2012 | Weeber et al. |
| 8,382,281 B2 | 2/2013 | Weeber |
| 8,388,137 B2 | 3/2013 | Dreher et al. |
| 8,430,508 B2 | 4/2013 | Weeber |
| 8,444,267 B2 | 5/2013 | Weeber et al. |
| 8,480,228 B2 | 7/2013 | Weeber |
| 8,500,805 B2 | 8/2013 | Kobayashi et al. |
| 8,506,075 B2 | 8/2013 | Bandhauer et al. |
| 8,529,623 B2 | 9/2013 | Piers et al. |
| 8,556,416 B2 | 10/2013 | Lawu |
| 8,556,417 B2 | 10/2013 | Das et al. |
| 8,573,775 B2 | 11/2013 | Weeber |
| 8,619,362 B2 | 12/2013 | Portney |
| 8,636,796 B2 | 1/2014 | Houbrechts et al. |
| 8,652,205 B2 | 2/2014 | Hong et al. |
| 8,678,583 B2 | 3/2014 | Cohen |
| 8,709,079 B2 | 4/2014 | Zhang et al. |
| 8,734,511 B2 | 5/2014 | Weeber et al. |
| 8,740,978 B2 | 6/2014 | Weeber et al. |
| 8,747,466 B2 | 6/2014 | Weeber et al. |
| 8,755,117 B2 | 6/2014 | Kobayashi et al. |
| 8,771,348 B2 | 7/2014 | Zhao |
| 8,827,446 B2 | 9/2014 | Iyer et al. |
| 8,906,089 B2 | 12/2014 | Piers et al. |
| 9,069,185 B2 | 6/2015 | Zhao |
| 9,078,745 B2 | 7/2015 | Zhang et al. |
| 9,122,074 B2 | 9/2015 | Piers et al. |
| 9,164,201 B2 | 10/2015 | Fermigier et al. |
| 9,223,148 B2 | 12/2015 | Fiala et al. |
| 9,304,329 B2 | 4/2016 | Zhao |
| 9,310,624 B2 | 4/2016 | Argal et al. |
| 9,320,594 B2 | 4/2016 | Schwiegerling |
| 9,329,309 B2 | 5/2016 | Van |
| 9,335,563 B2 | 5/2016 | Weeber |
| 9,335,564 B2 | 5/2016 | Choi et al. |
| 9,355,563 B2 | 5/2016 | Altintas et al. |
| 9,370,416 B2 | 6/2016 | Argal et al. |
| 9,518,864 B2 | 12/2016 | Grossinger et al. |
| 9,563,070 B2 | 2/2017 | Ando et al. |
| 9,622,856 B2 | 4/2017 | Weeber et al. |
| 9,869,580 B2 | 1/2018 | Grossinger et al. |
| 9,925,041 B2 | 3/2018 | Gerlach et al. |
| 9,931,200 B2 | 4/2018 | Van et al. |
| 10,698,234 B2 | 6/2020 | Zhao |
| 2001/0018612 A1 | 8/2001 | Carson et al. |
| 2002/0082690 A1 | 6/2002 | Sarbadhikari |
| 2002/0093701 A1 | 7/2002 | Zhang et al. |
| 2002/0105617 A1 | 8/2002 | Norrby et al. |
| 2002/0118337 A1 | 8/2002 | Perrott et al. |
| 2002/0122153 A1 | 9/2002 | Piers et al. |
| 2003/0014107 A1 | 1/2003 | Reynard |
| 2003/0063254 A1 | 4/2003 | Piers et al. |
| 2003/0076478 A1 | 4/2003 | Cox, I |
| 2003/0169491 A1 | 9/2003 | Bender et al. |
| 2003/0171808 A1 | 9/2003 | Phillips |
| 2004/0021824 A1 | 2/2004 | Ye et al. |
| 2004/0080710 A1 | 4/2004 | Wooley et al. |
| 2004/0085515 A1 | 5/2004 | Roffman et al. |
| 2004/0088050 A1 | 5/2004 | Norrby et al. |
| 2004/0106992 A1 | 6/2004 | Lang et al. |
| 2004/0111153 A1 | 6/2004 | Woods et al. |
| 2004/0138746 A1 | 7/2004 | Aharoni et al. |
| 2004/0150789 A1 | 8/2004 | Jones |
| 2004/0156014 A1 | 8/2004 | Piers et al. |
| 2004/0169820 A1 | 9/2004 | Dai et al. |
| 2004/0189981 A1 | 9/2004 | Ross et al. |
| 2004/0230299 A1 | 11/2004 | Simpson et al. |
| 2004/0246440 A1 | 12/2004 | Andino et al. |

(56) References Cited

U.S. PATENT DOCUMENTS

| | | |
|---|---|---|
| 2004/0252274 A1 | 12/2004 | Morris et al. |
| 2005/0057720 A1 | 3/2005 | Morris et al. |
| 2005/0096226 A1 | 5/2005 | Stock et al. |
| 2005/0099589 A1 | 5/2005 | Ishak |
| 2005/0128432 A1 | 6/2005 | Altmann |
| 2005/0203619 A1 | 9/2005 | Altmann |
| 2005/0259222 A1 | 11/2005 | Kelch et al. |
| 2005/0264757 A1 | 12/2005 | Morris et al. |
| 2005/0267575 A1 | 12/2005 | Nguyen et al. |
| 2006/0004446 A1 | 1/2006 | Aharoni et al. |
| 2006/0009816 A1 | 1/2006 | Fang et al. |
| 2006/0030938 A1 | 2/2006 | Altmann |
| 2006/0034003 A1 | 2/2006 | Zalevsky |
| 2006/0055883 A1 | 3/2006 | Morris et al. |
| 2006/0066808 A1 | 3/2006 | Blum et al. |
| 2006/0098162 A1 | 5/2006 | Bandhauer et al. |
| 2006/0098163 A1 | 5/2006 | Bandhauer et al. |
| 2006/0109421 A1 | 5/2006 | Ye et al. |
| 2006/0116763 A1 | 6/2006 | Simpson |
| 2006/0116764 A1 | 6/2006 | Simpson |
| 2006/0139570 A1 | 6/2006 | Blum et al. |
| 2006/0176572 A1 | 8/2006 | Fiala |
| 2006/0238702 A1 | 10/2006 | Glick et al. |
| 2006/0244904 A1 | 11/2006 | Hong et al. |
| 2006/0244905 A1 | 11/2006 | Piers et al. |
| 2007/0002444 A1 | 1/2007 | Piers et al. |
| 2007/0052920 A1 | 3/2007 | Stewart et al. |
| 2007/0129803 A1 | 6/2007 | Cumming et al. |
| 2007/0171362 A1 | 7/2007 | Simpson et al. |
| 2007/0182924 A1 | 8/2007 | Hong et al. |
| 2007/0236769 A1 | 10/2007 | Zalevsky |
| 2007/0258143 A1 | 11/2007 | Portney |
| 2007/0268451 A1 | 11/2007 | Raghuprasad |
| 2007/0282438 A1 | 12/2007 | Hong et al. |
| 2008/0030677 A1 | 2/2008 | Simpson |
| 2008/0147185 A1 | 6/2008 | Hong et al. |
| 2008/0161913 A1 | 7/2008 | Brady et al. |
| 2008/0161914 A1 | 7/2008 | Brady et al. |
| 2008/0269891 A1 | 10/2008 | Hong et al. |
| 2008/0273169 A1 | 11/2008 | Blum et al. |
| 2008/0300679 A1 | 12/2008 | Altmann |
| 2009/0062911 A1 | 3/2009 | Bogaert |
| 2009/0088840 A1 | 4/2009 | Simpson et al. |
| 2009/0164008 A1 | 6/2009 | Hong et al. |
| 2009/0187242 A1 | 7/2009 | Weeber et al. |
| 2009/0210054 A1 | 8/2009 | Weeber et al. |
| 2009/0234448 A1 | 9/2009 | Weeber et al. |
| 2009/0240328 A1 | 9/2009 | Treushnikov et al. |
| 2009/0295295 A1 | 12/2009 | Shannon et al. |
| 2009/0323020 A1 | 12/2009 | Zhao et al. |
| 2010/0014049 A1 | 1/2010 | Bandhauer et al. |
| 2010/0016961 A1 | 1/2010 | Hong et al. |
| 2010/0057202 A1 | 3/2010 | Bogaert |
| 2010/0087921 A1 | 4/2010 | Simpson |
| 2010/0097569 A1 | 4/2010 | Weeber et al. |
| 2010/0100177 A1 | 4/2010 | Zhao |
| 2010/0131060 A1 | 5/2010 | Simpson et al. |
| 2010/0161048 A1 | 6/2010 | Schaper, Jr. |
| 2010/0161051 A1 | 6/2010 | Hong |
| 2010/0274233 A1 | 10/2010 | Dick et al. |
| 2010/0281021 A1 | 11/2010 | Weeber et al. |
| 2010/0312336 A1 | 12/2010 | Hong et al. |
| 2010/0321635 A1 | 12/2010 | Apter et al. |
| 2011/0022170 A1 | 1/2011 | Simpson et al. |
| 2011/0098811 A1 | 4/2011 | Hong et al. |
| 2011/0109874 A1 | 5/2011 | Piers et al. |
| 2011/0125261 A1 | 5/2011 | Portney |
| 2011/0149236 A1 | 6/2011 | Weeber |
| 2011/0166652 A1 | 7/2011 | Bogaert et al. |
| 2011/0267693 A1 | 11/2011 | Kobayashi et al. |
| 2011/0270596 A1 | 11/2011 | Weeber |
| 2011/0292335 A1 | 12/2011 | Schwiegerling |
| 2011/0313522 A1 | 12/2011 | Hayes |
| 2011/0313523 A1 | 12/2011 | Hayes |
| 2011/0313525 A1 | 12/2011 | Cumming |
| 2011/0317124 A1 | 12/2011 | Weeber et al. |
| 2011/0317126 A1 | 12/2011 | Weeber |
| 2012/0029630 A1 | 2/2012 | Piers et al. |
| 2012/0059464 A1 | 3/2012 | Zhao |
| 2012/0140166 A1 | 6/2012 | Zhao |
| 2012/0143326 A1 | 6/2012 | Canovas et al. |
| 2012/0154740 A1 | 6/2012 | Bradley et al. |
| 2012/0165932 A1 | 6/2012 | Argal et al. |
| 2012/0170121 A1 | 7/2012 | Okada et al. |
| 2012/0283825 A1 | 11/2012 | Houbrechts et al. |
| 2012/0320335 A1 | 12/2012 | Weeber et al. |
| 2012/0323321 A1 | 12/2012 | Simonov et al. |
| 2013/0035760 A1 | 2/2013 | Portney |
| 2013/0046381 A1 | 2/2013 | Zalevsky et al. |
| 2013/0060330 A1 | 3/2013 | Weeber et al. |
| 2013/0107202 A1 | 5/2013 | Liang |
| 2013/0201445 A1 | 8/2013 | Das et al. |
| 2014/0172088 A1 | 6/2014 | Carson et al. |
| 2015/0022775 A1 | 1/2015 | Ando et al. |
| 2015/0029460 A1 | 1/2015 | Bradley et al. |
| 2015/0094807 A1 | 4/2015 | Piers et al. |
| 2015/0359625 A1 | 12/2015 | Argal et al. |
| 2016/0216535 A1 | 7/2016 | Zhao et al. |
| 2016/0220350 A1 | 8/2016 | Gerlach |
| 2016/0220352 A1 | 8/2016 | Choi et al. |
| 2016/0320633 A1 | 11/2016 | Weeber et al. |
| 2016/0334640 A1 | 11/2016 | De, Jr. et al. |
| 2016/0341978 A1 | 11/2016 | Schwiegerling |
| 2017/0172088 A1 | 6/2017 | May |
| 2017/0209259 A1 | 7/2017 | Choi et al. |
| 2017/0216020 A1 | 8/2017 | Weeber et al. |
| 2017/0219846 A1 | 8/2017 | Ando |
| 2017/0227789 A1 | 8/2017 | Ando et al. |
| 2017/0239038 A1 | 8/2017 | Choi et al. |
| 2017/0245985 A1 | 8/2017 | Canovas et al. |
| 2017/0245986 A1 | 8/2017 | Canovas et al. |
| 2017/0245987 A1 | 8/2017 | Canovas et al. |
| 2017/0252151 A1 | 9/2017 | Mackool |
| 2018/0092739 A1 | 4/2018 | Pagnoulle et al. |
| 2018/0132996 A1 | 5/2018 | Tiwari et al. |
| 2018/0147050 A1 | 5/2018 | Choi et al. |
| 2018/0147052 A1* | 5/2018 | Hong .................. A61F 2/1618 |
| 2018/0275428 A1 | 9/2018 | Ando |
| 2018/0373060 A1 | 12/2018 | Knox et al. |
| 2019/0004335 A1 | 1/2019 | Weeber et al. |
| 2019/0224000 A1 | 7/2019 | Choi et al. |
| 2019/0254810 A1 | 8/2019 | Tiwari et al. |
| 2019/0307557 A1 | 10/2019 | De Carvalho et al. |
| 2019/0314148 A1 | 10/2019 | Liu |
| 2020/0038172 A1 | 2/2020 | Hussain et al. |

FOREIGN PATENT DOCUMENTS

| | | |
|---|---|---|
| CA | 2507659 A1 | 6/2004 |
| CA | 2590085 A1 | 6/2006 |
| CN | 1951340 A | 4/2007 |
| CN | 101181171 B | 4/2011 |
| CN | 102665611 A | 9/2012 |
| DE | 69715830 T2 | 8/2003 |
| EP | 335731 A2 | 10/1989 |
| EP | 342895 A2 | 11/1989 |
| EP | 0343067 A1 | 11/1989 |
| EP | 355230 A2 | 2/1990 |
| EP | 0369561 A2 | 5/1990 |
| EP | 375291 A2 | 6/1990 |
| EP | 0393639 A2 | 10/1990 |
| EP | 412751 A2 | 2/1991 |
| EP | 0457553 A2 | 11/1991 |
| EP | 470811 A2 | 2/1992 |
| EP | 0537643 A1 | 4/1993 |
| EP | 605841 A1 | 7/1994 |
| EP | 0316162 B1 | 10/1995 |
| EP | 355230 B1 | 10/1995 |
| EP | 681198 A1 | 11/1995 |
| EP | 0537643 B1 | 3/1997 |
| EP | 0926531 A1 | 6/1999 |
| EP | 949529 A2 | 10/1999 |
| EP | 1376203 A2 | 1/2004 |
| EP | 1424049 A1 | 6/2004 |

(56) References Cited

FOREIGN PATENT DOCUMENTS

| | | |
|---|---|---|
| EP | 1862148 A1 | 12/2007 |
| EP | 1310267 B1 | 1/2008 |
| EP | 1891912 A1 | 2/2008 |
| EP | 2043558 A2 | 4/2009 |
| EP | 2045648 A1 | 4/2009 |
| EP | 1402308 B1 | 5/2009 |
| EP | 1424049 B1 | 6/2009 |
| EP | 2103279 A1 | 9/2009 |
| EP | 2113226 A1 | 11/2009 |
| EP | 2365379 A1 | 9/2011 |
| EP | 2377493 A1 | 10/2011 |
| EP | 2378319 A1 | 10/2011 |
| EP | 2290411 B1 | 5/2012 |
| EP | 2363097 B1 | 9/2012 |
| EP | 2527908 A1 | 11/2012 |
| EP | 2812882 A1 | 12/2014 |
| EP | 2813881 A1 | 12/2014 |
| EP | 2349093 B1 | 10/2015 |
| EP | 3150170 B1 | 12/2017 |
| IT | 1215851 B | 2/1990 |
| JP | 1154119 A | 6/1989 |
| JP | 2028615 A | 1/1990 |
| JP | 2079815 A | 3/1990 |
| JP | 2137814 A | 5/1990 |
| JP | 2249631 A | 10/1990 |
| JP | 3011315 A2 | 1/1991 |
| JP | 2000511299 A | 8/2000 |
| JP | 2003532157 A | 10/2003 |
| JP | 2010158315 A | 7/2010 |
| JP | 2013101323 A | 5/2013 |
| KR | 101154066 B1 | 6/2012 |
| RU | 2011154235 A | 7/2013 |
| RU | 2011154238 A | 7/2013 |
| WO | 9002963 A1 | 3/1990 |
| WO | 9222264 A1 | 12/1992 |
| WO | 9303409 A1 | 2/1993 |
| WO | 9413225 A1 | 6/1994 |
| WO | 9417435 A1 | 8/1994 |
| WO | 9724639 A1 | 7/1997 |
| WO | 9744689 A1 | 11/1997 |
| WO | 9831299 A2 | 7/1998 |
| WO | 9907309 A1 | 2/1999 |
| WO | 9923526 A1 | 5/1999 |
| WO | 0019906 A1 | 4/2000 |
| WO | 0076426 A2 | 12/2000 |
| WO | 0121061 A1 | 3/2001 |
| WO | 0163344 A1 | 8/2001 |
| WO | 0182839 A1 | 11/2001 |
| WO | 0189424 A1 | 11/2001 |
| WO | 0221194 A2 | 3/2002 |
| WO | 0234158 A2 | 5/2002 |
| WO | 02084381 A2 | 10/2002 |
| WO | 02088830 A1 | 11/2002 |
| WO | 03009053 A1 | 1/2003 |
| WO | 2004013680 A1 | 2/2004 |
| WO | 2004034129 A1 | 4/2004 |
| WO | 2004049979 A1 | 6/2004 |
| WO | 2004090611 A2 | 10/2004 |
| WO | 2004096014 A2 | 11/2004 |
| WO | 2004113959 A2 | 12/2004 |
| WO | 05019906 A1 | 3/2005 |
| WO | 06025726 A1 | 3/2006 |
| WO | 2006047698 A1 | 5/2006 |
| WO | 06060477 A2 | 6/2006 |
| WO | 2006060480 A2 | 6/2006 |
| WO | 2006067255 A1 | 6/2006 |
| WO | 2007092948 A1 | 8/2007 |
| WO | 2007133384 A2 | 11/2007 |
| WO | 2008045847 A2 | 4/2008 |
| WO | 2008150982 A1 | 12/2008 |
| WO | 2009017403 A1 | 2/2009 |
| WO | 2009027438 A2 | 3/2009 |
| WO | 2009043985 A1 | 4/2009 |
| WO | 2009058755 A1 | 5/2009 |
| WO | 2009076670 A1 | 6/2009 |
| WO | 2009130610 A2 | 10/2009 |
| WO | 2009148454 A1 | 12/2009 |
| WO | 2010046356 A1 | 4/2010 |
| WO | 2010054255 A1 | 5/2010 |
| WO | 2010059764 A1 | 5/2010 |
| WO | 2010079528 A1 | 7/2010 |
| WO | 2010093975 A2 | 8/2010 |
| WO | 2010100523 A1 | 9/2010 |
| WO | 2010104530 A1 | 9/2010 |
| WO | 2010144315 A1 | 12/2010 |
| WO | 2011024125 A1 | 3/2011 |
| WO | 2011055228 A2 | 5/2011 |
| WO | 2011075641 A2 | 6/2011 |
| WO | 2011075668 A1 | 6/2011 |
| WO | 2012004746 A2 | 1/2012 |
| WO | 2012031211 A1 | 3/2012 |
| WO | 2012070313 A1 | 5/2012 |
| WO | 2012078763 A1 | 6/2012 |
| WO | 2012085917 A1 | 6/2012 |
| WO | 2012122411 A1 | 9/2012 |
| WO | 2012140389 A1 | 10/2012 |
| WO | 2013018379 A1 | 2/2013 |
| WO | 2013028992 A1 | 2/2013 |
| WO | 2013093916 A1 | 6/2013 |
| WO | 2013114209 A2 | 8/2013 |
| WO | 2013116133 A1 | 8/2013 |
| WO | 2013118177 A1 | 8/2013 |
| WO | 2013118499 A1 | 8/2013 |
| WO | 2014008343 A1 | 1/2014 |
| WO | 2014033543 A2 | 3/2014 |
| WO | 2014091528 A1 | 6/2014 |
| WO | 2014111831 A1 | 7/2014 |
| WO | 2014189049 A1 | 11/2014 |
| WO | 2017137841 A1 | 8/2017 |
| WO | 2017149403 A1 | 9/2017 |
| WO | 2018093873 A1 | 5/2018 |
| WO | 2018150236 A1 | 8/2018 |
| WO | 2019130030 A1 | 7/2019 |
| WO | 2020115104 A1 | 6/2020 |

OTHER PUBLICATIONS

Seitz B., et al, "Corneal Topography," Current Opinion in Ophthalmolgy, 1997, vol. 8 (4), pp. 8-24.

Siedlecki D., et al., "Radial Gradient index Intraocular Lens: a Theoretical Model," Journal of Modern Optics, Feb. 20-Mar. 10, 2008, vol. 55 (4-5), pp. 639-647.

Smith G. et al., "The spherical aberration of the crystalline lens of the human eye," Vision Res., 2001, 41 (2), 235-243.

Smith Kinney, "Sensitivity of the eye to spectral radiation at scotopic and mesopic intensity levels," Journal of the Optical Society of America, 1955, 45 (7), 507-514.

Terwee T., et al., "Visualization of the Retinal Image in an Eye Model With Spherical and Aspheric, Diffractive, and Refractive Multifocal Intraocular Lenses," Journal of Refractive Surgery, Mar. 2008, vol. 24 (3), pp. 223-232.

Thibos L. N. et al., "The chromatic eye: a new reduced-eye model of ocular chromatic aberration in humans," Applied Optics, 1992, 31 (19), 3594-3600.

Thibos L. N. et al., "Theork and measurement of ocular chromatic aberration," Vision Res, 1988, 30 (1), 33-49.

Townsley, "New Knowledge of the corneal contour," Contacto, 1970, pp. 38-43.

Van Den Berg T.J., "Analysis of Intraocular Straylight, Especially in Relation to Age," Optometry and Vision Science, Feb. 1995, vol. 72 (2), pp. 52-59.

Van Meeteren A., "Calculations on the Optical Modulation Transfer Function of the Human Eye for White Light," Optica Acta, May 1974, vol. 21 (5), pp. 395-412.

Verriest G., "The Spectral Curve of Relative Luminous Efficiency in Different Age Groups of Aphakic Eyes," Mod Probl Ophthalml., 1974, 13, 314-317.

Villegas E.A., et al., "Correlation between Optical and Psychophy, Sical Parameters as a Function of Defocus," Optometry and Vision Science, Jan. 1, 2002, vol. 79 (1), pp. 60-67.

(56) References Cited

OTHER PUBLICATIONS

Wang J.Y., et al, "Wave-Front Interpretation With Zernike Polynomials," Applied Optics, 1980, vol. 19 (9), pp. 1510-1518.
International Search Report and Written Opinion for Application No. PCT/EP2018/056744, dated Jun. 14, 2018, 16 pages.
Albert D.M., "(Book Review) Intraocular Lenses: Evolution, Designs, Complications, and Pathology, by David Apple et al.," Archieves of Opthalmology, 1990, vol. 108, pp. 650.
Alfonso J.F., et al., "Prospective Study of the Acri.LISA Bifocal Intraocular Lens," Journal of Cataract Refractive Surgery, Nov. 2007, vol. 33 (11), pp. 1930-1935.
Alvarez S. L. et al., "Spectral threshold: measurement and clinical applications," British Journal of Ophthalmology, 1983, 67, 504-507.
Apple D.J., et al., Eds., "Intraocular Lenses: Evolution, Designs, Complications and Pathology," in: New Concepts in Intraocular Lens Implantation, Williams & Wilkins publisher, Jan. 1989, vol. 22 (36), pp. 205-221.
Apple D.J., et al., Eds., "Intraocular Lenses: Evolution, Designs, Complications and Pathology," in: New Concepts in Intraocular Lens Implantation, Williams & Wilkins publisher, Jan. 1989, vol. 36 (1), pp. 21-36.
Artal P., et al., "Contributions of the Cornea and the Lens to the Aberrations of the Human Eye," Optics Letters, 1998, vol. 23 (21), pp. 1713-1715.
Atchinson D.A., "Design of Aspheric Intraocular Lens," Ophthamic & Physiological Optics, 1991, vol. 11 (2), pp. 137-146.
Atchinson D.A., et al., "Optical Design of Intraocular Lenses. II. Off-Axis performance," Optometry & Vision Science, 1989, vol. 66 (9), pp. 579-590.
Atchinson D.A., et al., "Third-Order Aberrations Of Pseudophakic Eyes," Ophthalmic and Physiological Optics , 1989, vol. 9, pp. 205-211.
Atchinson D.A., "Optical Design of Intraocular Lenses. I. On-Axis Performance," American Academy of Optometry, 1989, vol. 66 (8), pp. 492-506.
Atchinson D.A., "Optical design of intraocular lenses III. On-Axis Performance in the Presence of Lens Displacement," American Academy of Optometry, 1989, vol. 66 (10), pp. 671-681.
Atchinson, "Refractive errors induced by displacement of intraocular lenses within the pseudophakic eye," Optometry & Vision Science, 1989, 66 (3), 146-152.
Bonnet R., et al, "New Method Of Topographical Ophthalmometry—Its Theoretical And Clinical Applications," American Journal of Optometry, 1962, vol. 39 (5), pp. 227-251.
Bradley A. et al., "Achromatizing the Human Eye" Optometry & Vision Science, 1991, vol. 68 (8), pp. 608-616.
Buralli D.A., et al, "Optical Performance Of Holographic Kinoforms," Applied Optics, Mar. 1989, vol. 28 (5), pp. 976-983.
Canovas C., et al., "Hybrid Adaptive-Optics Visual Simulator," Optical Letters, Jan. 15, 2010, vol. 35 (2), pp. 196-198.
Cohen A.L., "Diffractive Bifocal Lens Design," Optometry and Vision Science, Jun. 1993, vol. 70 (6), pp. 461-468.
Cohen A.L., "Practical Design of a Bifocal Hologram Contact Lens or Intraocular Lens," Applied Optics, Jul. 1, 1992, vol. 31 (19), pp. 3750-3754.
Diffractive Lenses for Extended Depth of Focus and Presbyopic Correction, Presentation from Wavefront Congress held on Feb. 15, 2008, Rochester, New York.
Doskolovich L.L., et al., "Special Diffractive Lenses," Lens and Optical Systems Design, Apr. 1992, vol. 1780, pp. 393-402.
Dwyer W. O. et al., "Racial Differences In Color Vision: Do They Exist", American Journal of Optometry & Physiological Optics, 1975, 52, 224-229.
El Hage S.G., et al., "Contribution of the Crystalline Lens to the Spherical Aberration of the Eye," 1973, vol. 63 (2), pp. 205-211.
Futhey J.A., "Diffractive Bifocal Intraocular Lens," SPIE, 1989, vol. 1052, pp. 142-148.
Geun Y., et al., "Visual Performance after Correcting the Monochromatic and Chromatic Aberrations of the Eye," Journal of the Optical Society of America, 2002, vol. 19 (2), pp. 266-275.

Glasser A. et al., "Presbyopia and the optical changes in the human crystalline lens with age," Vision Res, 1998, 38 (2), 209-229.
Greivenkamp J.E., et al., "Visual Acuity Modeling Using Optical Raytracing Of Schematic Eyes," American Journal of Ophthalmology, 1995, vol. 120 (2), pp. 227-240.
Griswold Scott et al., "Scotopic Spectral Sensitivity of Phakic and Aphakic Observers Extending into the Near Ultraviolet," Vision res, 1992, 32 (9), 1739-1743.
Guirao A., et al., "Corneal Wave Aberration from Videokeratography: Accuracy And Limitations of the Procedure," Journal of the Optical Society of America, 2000, vol. 17 (6), pp. 955-965.
Iovs, 1999, 40 (4), S535.
Kiely et al., "The mean shape of the human cornea," Optica ACTA, 1982, 29 (8), 1027-1040.
Kokoschka S., et al., "Influence of Field Size on the Spectral Sensitivity of the Eye in the Photopic and Mesopic Range," American Journal of Optometry and Physiological Optics, 1985, vol. 62 (2), pp. 119-126.
Liang J., et al, "Objective Measurement Of Wave Aberrations Of The Human Eye With The Use Of A Hartmann-Shack Wave-Front Sensor," Journal of the Optical Society of America, 1994, vol. 11 (7), pp. 1949-1957.
Lindsay R., et al., "Descriptors of Corneal Shape," Optometry and Vision Science, 1998, vol. 75 (2), pp. 156-158.
Liou H.L., et al., "Anatomically Accurate, Finite Model Eye for Optical Modeling," Journal of Optical Society of America, Aug. 1997, vol. 14 (8), pp. 1684-1695.
Lotmar, "Theoretical eye model with aspherics," Journal of the Optical Society of America, 1971, 61 (11), 1522-1529.
Malacara D., et al., "Wavefront Fitting With Discrete Orthogonal Polynomials In a Unit Radius Circle," Optical Engineering, 1990, vol. 29 (6), pp. 672-675.
Mandell R.B., et al., "Mathematical Model of the Corneal Contour," 1965, School of Optometry, University of California, Berkeley, pp. 183-197.
Marcos S., et al., "A New Approach to the Study of Ocular Chromatic Aberrations," Vision Research, 1999, vol. 39 (26), pp. 4309-4323.
Marsack J.D., et al., "Metrics of Optical Quality Derived from Wave Aberrations Predict Visual Performance," Journal of Vision, Apr. 2004, vol. 4 (4), pp. 322-328.
Monsoriu J.A., et al., "Devil's Lenses," Optics Express, Oct. 17, 2007, vol. 15 (21), pp. 13858-13864.
Mordi J.A., et al., "Influence of Age of Chromatic Aberration of the Human Eye," American Journal of Optometry & Physiological Optics, 1985, vol. 62 (12), pp. 864-869.
Morlock, R., et al., "Patient-Reported Spectacle Independence Questionnaire (PRSIQ): Development and Validation," American Journal of Ophthalmology, Jun. 2017, vol. 178, pp. 101-114.
Navarro R., et al., "Accommodation-Dependent Model of the Human Eye with Aspherics," Journal of the Optical Society of America, Aug. 1985, vol. 2 (8), pp. 1273-1281.
Norrby S., et al., "Model Eyes for Evaluation of Intraocular Lenses," Applied Optics, Sep. 7, 2007, vol. 46 (26), pp. 6595-6605.
"Optical Design," Military Standardization Handbook, 1962, Chapter 4, U.S. Department of Defense MIL-HDBK-141, 4-1-4-19.
Oshika T., et al., "Changes in Corneal Wavefront Aberrations with Aging," Investigative Ophthalmology & Visual Science, 1999, vol. 40 (7), pp. 1351-1355.
Patel S., et al., "Shape and Radius of Posterior Corneal Surface," Refractive and Corneal Surgery, 1993, vol. 9 (3), pp. 173-181.
Piers P.A., et al., "Eye Models for the Prediction of Contrast Vision in Patients with New Intraocular Lens Designs," Optics Letters, Apr. 1, 2004, vol. 29 (7), pp. 733-735.
Piers P.A., et al., "Theoretical Comparison of Aberration-Correcting Customized and Aspheric Intraocular Lenses," Journal of Refractive Surgery, Apr. 2007, vol. 23 (4), pp. 374-384.
Said et al., "The Variation with Age of the Spectral Transmissivity of the Living Human Crystalline Lens," Gerontologia, 1959, 213-231.
Guillon M., et al., "Corneal Topography: A Clinical Model," Ophthalmic & Physiological Optics, 1986, vol. 6 (1), pp. 47-56.

(56) References Cited

OTHER PUBLICATIONS

Smith G., et al., "The spherical aberration of intra-ocular lenses," Department of Optometry, 1988, vol. 8 (3), pp. 287-294.
Castignoles F., et al., "Comparison of the Efficiency, MTF and Chromatic Properties of Four Diffractive Bifocal Intraocular Lens Designs," Optics Express, Mar. 2010, vol. 18 (5), pp. 5245-5256.
Sokolowski M., et al. "Hybrid Heptafocal Intraocular Lenses," Optica Applicata, Dec. 2015, vol. 45 (3), pp. 285-298.

* cited by examiner

DIFFRACTIVE INTRAOCULAR LENSES FOR EXTENDED RANGE OF VISION

CROSS-REFERENCE TO RELATED APPLICATIONS

This application claims priority to U.S. Provisional Patent Application No. 62/473,200, filed Mar. 17, 2017, which is incorporated herein by reference in its entirety.

BACKGROUND

Embodiments of the present disclosure relate generally to ophthalmic lenses, such as intraocular lenses (IOLs), and particular embodiments provide methods, devices, and systems for mitigating or treating vision conditions such as presbyopia via ophthalmic lenses.

SUMMARY

Embodiments herein described include an ophthalmic lens with a first surface and a second surface disposed about an optical axis, the lens being characterized by a depth of focus across a range of optical powers, i.e. an extended depth of focus (EDOF) that achieves an extended range of vision (ERV). A diffractive profile is imposed on one of the surfaces and configured to cause a distribution of non-negligible amounts of light among the depth of focus. The diffractive profile includes at least a central zone with at least one central diffractive echelette having a first phase delay, and a peripheral zone comprising at least one peripheral diffractive echelette having a second phase delay less than the first phase delay. In some embodiments, a third, intermediate zone may also be provided comprising at least one intermediate diffractive echelette having a third phase delay less than the first phase delay.

The central zone operates primarily in a higher diffractive order than the peripheral zone; and may also operate in a higher diffractive order than an optional intermediate zone. The incorporation of the central diffractive zone in the lens provides the combined diffractive profile (central zone+peripheral zone) with a longer depth of focus than that achieved by a diffractive profile defined just by the peripheral zone; and provides a longer depth of focus than a diffractive profile defined by the peripheral and an optional intermediate zone. The peripheral zone and/or optional intermediate zones may operate primarily in the first and/or second diffractive orders and distribute light to the far and intermediate ranges of viewing distances; while the central zone, which operates primarily in the second or third diffractive orders, distributes light primarily to the intermediate and/or near ranges of viewing distances. In combination, the combination of the central, peripheral, and optional intermediate diffractive zones provide light to an extended range of viewing distances. Embodiments also provide for high total light efficiency, in some cases capturing more than 90% of incident light in the complete range of vision. Embodiments also correct or partially correct for chromatic aberration in the range of vision.

DETAILED DESCRIPTION

Figure 1:
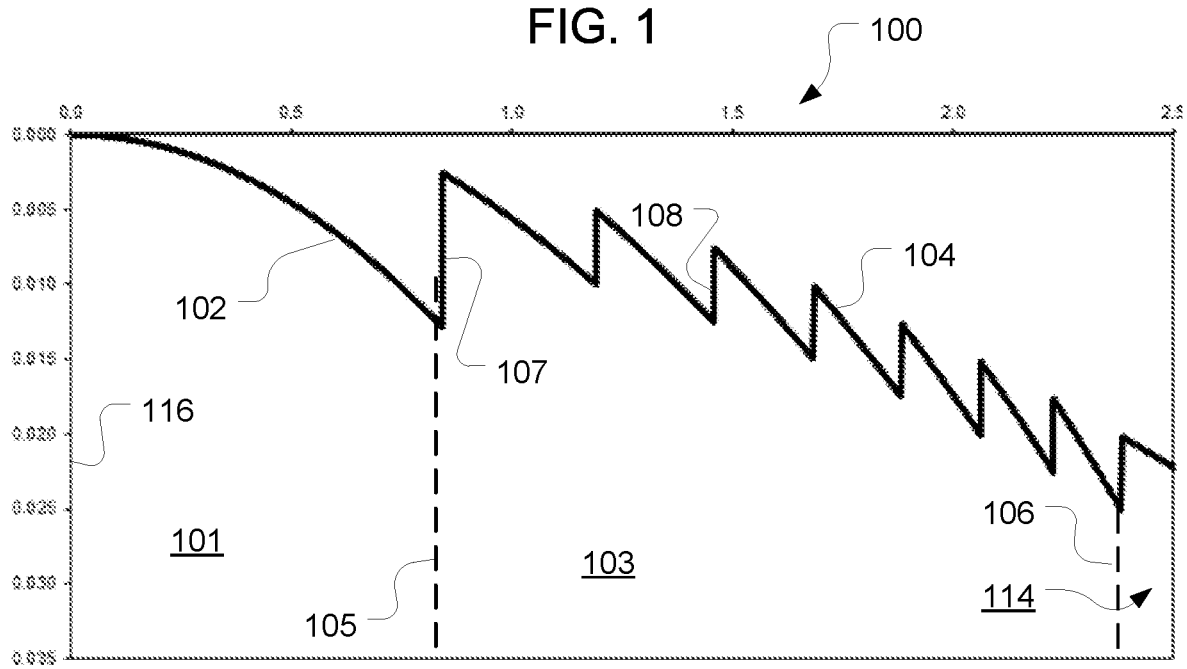
FIG. 1 is a graphical representation of a first example diffractive lens profile showing a central diffractive zone having one diffractive echelette, and a peripheral diffractive zone, according to some embodiments of the present invention.

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Embodiments herein disclosed relate to diffractive intraocular lenses for providing extended depth of focus to a patient (ERV lenses). According to some embodiments, an intraocular lens can include a diffractive profile having a central diffractive zone that works in a higher diffractive order than a remainder of the diffractive profile. Suitable diffractive lenses can have a light efficiency (i.e., total light passed to the diffractive orders as a percentage of incident light) of approximately 90%, distributed over a defocus range that covers at least three different diffractive orders within the visual range, and with at least a non-zero or non-negligible percentage of light distributed to each diffractive order. According to some embodiments, a diffractive lens can partially correct for ocular chromatic aberration. In alternative embodiments, the diffractive lens can fully correct or over-correct for ocular chromatic aberration.

Embodiments of lenses herein disclosed can be configured for placement in the eye of a patient and aligned with the cornea to augment and/or partially replace the function of the cornea. In some embodiments, corrective optics may be provided by phakic IOLs, which can be used to treat patients while leaving the natural lens in place. Phakic IOLs may be angle supported, iris supported, or sulcus supported. IOLs can be further secured with support members that attach the IOL to the eye, e.g., with physical extensions from the IOL into adjacent corneal or iris tissue. Phakic IOLs can also be placed over the natural crystalline lens or piggy-backed over another IOL. Exemplary ophthalmic lenses include contact lenses, phakic lenses, pseudophakic lenses, corneal inlays, and the like. It is also envisioned that the lens shapes disclosed herein may be applied to inlays, onlays, accommodating IOLs, spectacles, and even laser vision correction.

As used herein, non-zero may refer generally to a non-negligible or non-trivial amount of light, typically at least 10% of the total light passing through the lens for IOLs.

Embodiments disclosed herein can provide an extended depth of focus. In some embodiments, diffractive intraocular lenses herein can provide better distance, intermediate, and/or near image quality than presently available multifocal lenses while mitigating certain dysphotopsia effects, such as glare or halo.

Methods of manufacture for diffractive lenses as disclosed herein, as well as methods of treatment utilizing said diffractive lenses, may include techniques described in, e.g., U.S. Pat. No. 9,335,563, entitled "MULTI-RING LENS, SYSTEMS AND METHODS FOR EXTENDED DEPTH OF FOCUS," which is hereby incorporated by reference.

Diffractive lenses can make use of a material having a given refractive index and a surface curvature which provide a refractive power. Diffractive lenses have a diffractive profile which confers the lens with a diffractive power or power profile that may contribute to the base power of the lens. The diffractive profile is typically characterized by a number of diffractive zones. When used for ophthalmic lenses these diffractive zones are typically annular lens zones, or echelettes, spaced about the optical axis of the lens. Each echelette may be defined by an optical zone, a transition zone between the optical zone and an optical zone of an adjacent echelette, and echelette geometry. The echelette geometry includes an inner and outer diameter and a shape or slope of the optical zone, a height or step height, and a shape of the transition zone. The surface area or diameter of the echelettes largely determines the diffractive power profile of the lens and the step height of the transition between echelettes largely determines the light distribution within the diffractive power profile. Together, these echelettes form a diffractive profile.

ERV intraocular lenses (IOLs) are intended to provide a patient with improved vision in a range of distances, covering near, intermediate and far vision. Near range of vision may generally correspond to vision provided when objects are at distances from about 33 up to 60 cm from a subject eye with the image substantially focused on the subject retina, and may correspond to a vergence of approximately −1.6 D to −3 D. Intermediate range of vision may generally correspond to vision for objects at a distance between 63 cm up to 1.3 m from a subject eye with the image substantially focused on the subject retina, and may correspond to a vergence of approximately −1.6 D to −0.75 D. Far range of vision may generally correspond to vision for objects at any distance greater than about 1.3 m from a subject eye with the image substantially focused on the subject retina, and may correspond to a vergence of less than −0.75 D. In the case of an ERV lens, or a lens having an extended depth of focus, the diffractive profile can provide a plurality of focal lengths that overlap across a range of optical powers to provide good visual acuity throughout the extended depth of focus.

A traditional multifocal diffractive profile on a lens may be used to mitigate presbyopia by providing two or more optical powers, for example, one for near vision and one for far vision. The diffractive lenses disclosed herein provide an extended depth of focus across a range of optical powers. The concepts disclosed here apply to both ERV lenses and multifocal lenses. The lenses may also take the form of an intraocular lens placed within the capsular bag of the eye, replacing the original lens, or placed in front of the natural crystalline lens. The lenses may be in the form of a contact lens, most commonly a contact lens that extends the depth of focus, or in any other form mentioned herein.

In some embodiments, a diffractive profile can include multiple diffractive zones, e.g., a central zone that includes one or more echelettes, and a peripheral zone beyond the central zone having one or more peripheral echelettes. In some specific embodiments, an intermediate diffractive zone between the central and peripheral zones may be added to the diffractive profile. Each diffractive zone may include some form of apodization. In this context, apodization means that the light distribution gradually varies between adjacent echelettes, but light remains directed to the same non-negligible diffractive orders for all echelettes within the zone. In some specific embodiments, a refractive zone may be added to a lens surface outside of the peripheral diffractive zone. In some other embodiments one or more of the diffractive zones comprise apodized diffractive surfaces. The diffractive properties of each component echelette of a diffractive zone or diffractive profile are caused by the physical parameters of the component echelettes, e.g. step height, shape, and width. A single echelette can be characterized by its phase delay, a phase delay of a zone can be characterized by the individual phase delays of its component echelettes, and a phase delay of a lens profile can be characterized by the phase delays of the echelettes and/or zones within the profile.

FIG. 1 is a graphical representation of an example lens profile 100 having a central echelette 102 that defines a central diffractive zone 101 and multiple peripheral echelettes 104 that define a peripheral diffractive zone 103 of the lens. In some embodiments, a refractive zone 114 can extend outside of the peripheral diffractive zone 103. The central diffractive zone 101 extends from a lens center 116 to the central zone boundary 105. The peripheral zone 103 extends from the central zone boundary 105 to the peripheral zone boundary 106. The specific example provides seven peripheral echelettes 104; however, lenses may have more or fewer echelettes in the peripheral zone without deviating significantly from this disclosure. The specific lens profile shown is described below in Table 1. Positions are shown in terms of the diffractive zone boundary relative to the lens center. The position of each particular echelette is determined by the position of the first echelette (e.g. 0.84 mm in the example at Table 1, below,) multiplied by the squared root of the echelette number.

TABLE 1

Diffractive lens profile 100 (FIG. 1)

| Zone | # of Echelettes | Phase Delay (λ) | Step Height (μM) | Position (mm) |
|---|---|---|---|---|
| Central (101) | 1 | 2.51 | 10.3 (107) | 0.84 (105) |
| Peripheral (103) | 7 | 1.2 | 4.9 (108) | 2.38 (106) |
| Refractive (114) | 0 | 0 | 0 | >2.38 (114) |

The diffractive lens profile 100 shown in FIG. 1 features a central diffractive zone 101 defined by a single central echelette 102 that has a larger phase delay than the remaining echelettes (approximately 2.51λ). The central zone 101 is joined to the peripheral zone 103 by a step height 107 that can be different, and in some cases larger, than the step heights 108 separating echelettes in the peripheral zone. Phase delay is defined in terms of the period of the design wavelength, in this case 550 nm. Phase delay is the difference in phase between the light having passed through two adjacent echelettes. By virtue of the high phase delay, this central echelette operates primarily in the $2^{nd}$ and $3^{rd}$ diffractive orders, which directs light predominantly toward the intermediate and near visual ranges. The diffractive profile outside the central zone, i.e. the peripheral echelettes 104, operate predominantly in the $1^{st}$ and 2nd diffractive orders, the $1^{st}$ diffractive order adding light to the far focal range for distance vision.

The diffractive profile partially corrects chromatic aberration induced by the ocular media and/or the lens material in the range of vision provided by the lens. The distributions of light obtained by the components of the example lens 100, and by the total lens, are shown below in Table 2. Table 2 refers the light distribution at the far visual range (i.e. by the first diffractive order) as well as to the light distribution within the complete visual range provided by the diffractive profile (i.e. distance and extended depth of focus). This complete visual range is herein defined as the combination of the first, second and third diffractive orders. In alternative embodiments, the visual range can also include the light distribution for the fourth diffractive order.

TABLE 2

Light distributions of example lens profile 100

| Order | 1 (Far) | Visual Range |
|---|---|---|
| Peripheral | 0.85 | 0.94 |
| Central + Peripheral | 0.60 | 0.92 |

By way of comparison, a bifocal lens typically has a light loss of less than 20% of incident light (e.g., in some cases, of about 18% of incident light). Thus, the example ERV diffractive lens profile 100, which has a light loss of only about 8%, loses less than half as much light as a standard multifocal lens. Furthermore, a typical multifocal bifocal profile with a 50:50 light distribution between distance and near provides with 40% of light for distance vision. The example at Table 2 provides a 20% more light for far, with having a total of 60% light directed to distance.

Figure 2:
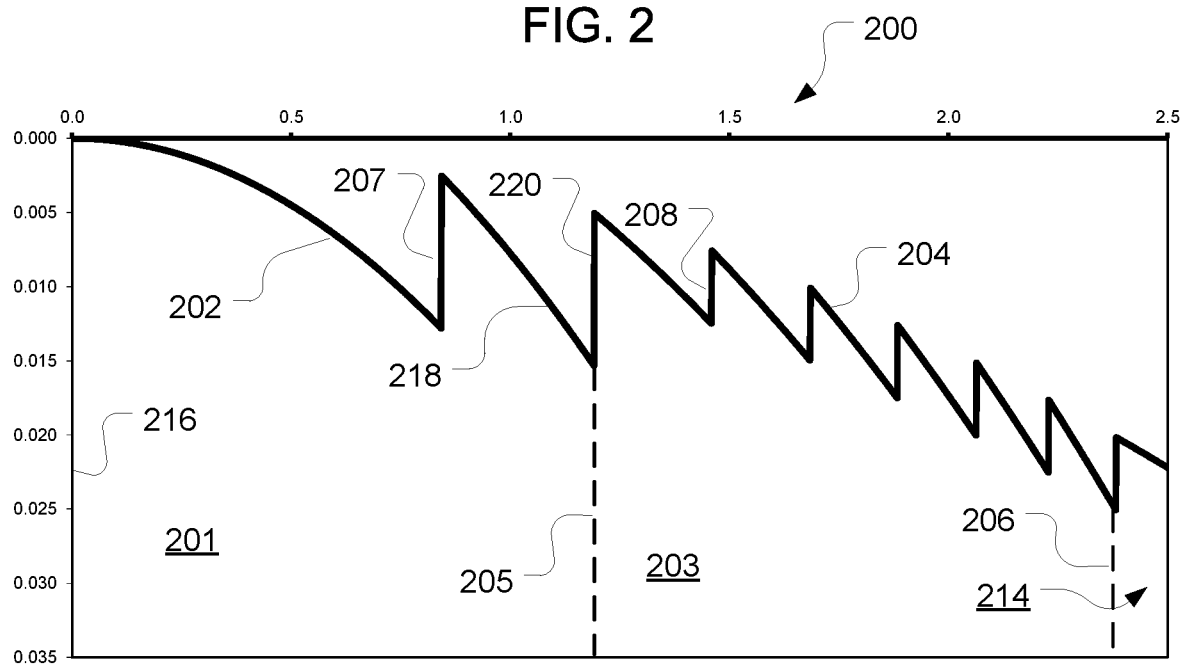
FIG. 2 is a graphical representation of a second example diffractive lens profile showing a central diffractive zone having multiple diffractive echelettes, and peripheral diffractive zone, according to some embodiments of the present invention.

In alternative embodiments, a lens may have a central diffractive zone defined by multiple diffractive echelettes rather than a single diffractive echelette. FIG. 2, for example, illustrates a diffractive lens profile 200 that is similar to the diffractive lens profile 100, with an expanded central zone 201 having a first central echelette 202 and a second central echelette 218 separated by a central step height 207. A peripheral zone 203 is characterized by peripheral echelettes 204 separated by step heights 208, the peripheral zone ending at a peripheral zone boundary 206. Optionally, a refractive periphery 214 may extend beyond the peripheral zone boundary 206. In this example profile, the central diffractive zone 201 is connected with the peripheral zone 203 by a transition step height 220, which is similar to the transition step height 107. According to embodiments, the example lens profile 200 can also achieve an extended depth of focus as the diffractive lens profile 100, and in some cases may further increase light directed to the 2nd and 3rd diffractive order.

Figure 3:
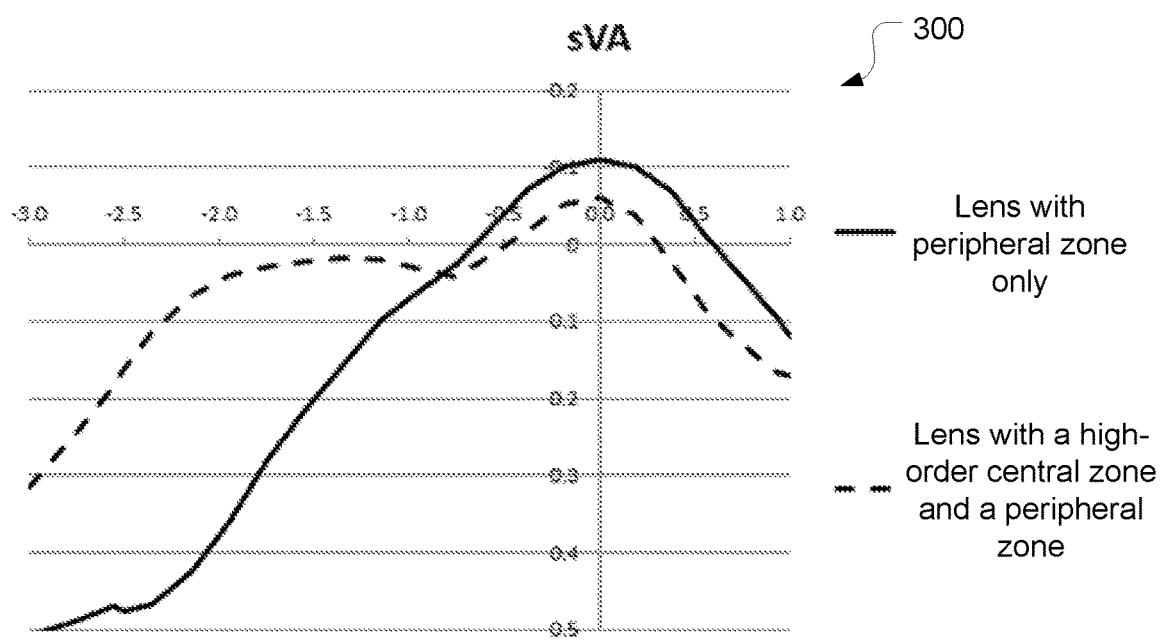
FIG. 3 is a graphical representation of simulated visual acuity of an example diffractive lens according to FIG. 1 compared to a diffractive lens having only a peripheral diffractive profile, according to some embodiments of the present invention.

FIG. 3 shows a graphical representation of simulated visual acuities 300 of the example lens 100 and a sibling diffractive design in which all echelettes have the same step heights a the peripheral component as shown in Tables 1, above. The calculations of simulated visual acuity were performed according the methods described in Aixa Alarcon, Carmen Canovas, Robert Rosen, Henk Weeber, Linda Tsai, Kendra Hileman, and Patricia Piers, "Preclinical metrics to predict through-focus visual acuity for pseudophakic patients," Biomed. Opt. Express 7, 377-1888 (2016). The example simulated visual acuities 300 illustrate that the incorporation of the central zone extends the depth of focus with respect to that provided by the echelettes with steps heights that define the peripheral zone by approximately 1 D (i.e., referring to the defocus range with a visual acuity over a threshold of about 0.2 Log MAR).

In some (general) embodiments, the phase delay in the central echelette can be larger than 2λ and smaller than 4λ. In specific embodiments, phase delay can range from about 2.3λ up to 3.5λ, or from 2.45λ to 3.2λ, or from 2.5λ to 2.95λ. The number of echelettes is determined based on the desired geometry of each echelette and the available radius. The number of echelettes may vary from as few as 8 to up to 32 in some specific embodiments within a lens diameter of 6 mm. In specific embodiments, the first echelette may be positioned with an echelette boundary between 0.5 and 0.9 mm from a center of the lens, with a remainder of the echelettes placed according the position of the first echelette multiplied by the square root of the echelette number. In some embodiments, the phase delay of the peripheral echelettes can range from 1λ and can be smaller than 2λ. In specific embodiments, phase delay can range from about 1λ up to 1.5λ, or from 1.2λ to 1.5λ, or from 1.336λ to 1.5λ.

Various peripheral diffractive zone profiles may be combined with an elevated central profile to achieve different specific lens prescriptions. For example, various alternative embodiments of peripheral diffractive lens profiles are shown below in Table 3.

TABLE 3

Alternative examples of diffractive lens profiles with varying peripheral zones

| Zone | # of Echelettes | Phase Delay (λ) | Step Height (μM) | Position (mm) |
|---|---|---|---|---|
| Central 1 | 1 | 2.51 | 10.3 | 0.84 |
| Peripheral 1 | 7 | 1 | 4.1 | 2.38 |
| Peripheral 3 | 7 | 1.366 | 5.6 | 7.38 |

These peripheral zones can be combined with a central zone like described in Table 1. Therefore, the step height of the central zone is constant across the examples; and the step heights and phase delays of the diffractive echelettes in the peripheral zone are modified. In each example, the peripheral echelettes have the same step heights across the zone, which vary between 4.1 and 5.6 microns. The position of the echelettes in each peripheral diffractive profile is determined in the same way for each example combination (i.e. the position of one particular echelette is that of the central multiplied by the square root of the echelette number).

Figure 4:
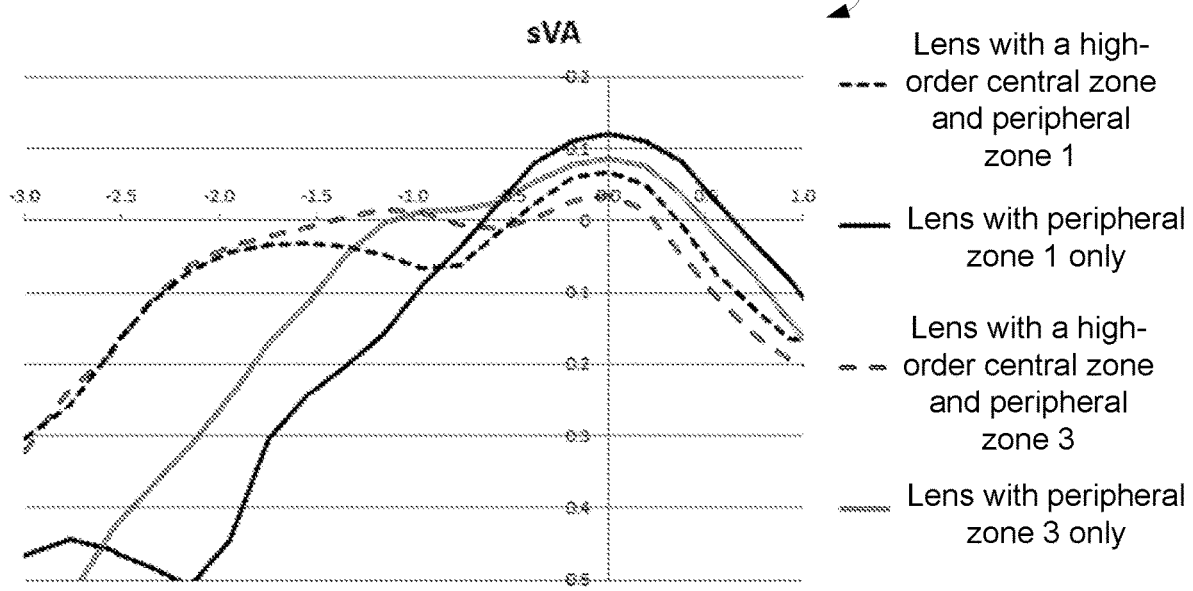
FIG. 4 is a graphical representation of simulated visual acuity of example diffractive lenses having multiple combinations of central and peripheral diffractive zones, according to some embodiments of the present invention.

FIG. 4 shows a graphical representation of simulated visual acuities 400 of the example lenses of Table 3, above as compared to these of the sibling diffractive designs in which all echelettes have the same step heights as the peripheral component 1 and 3 respectively, as shown in Table 3. In all the cases, the combination with the higher order central echelette provides a longer depth of focus than the peripheral profile alone. The example simulated visual acuities 400 illustrate that, by varying the phase delays and step heights of the peripheral echelettes, a lens can be tuned to provide greater visual acuity at intermediate or distance, depending on the desired prescription of the lens.

In some embodiments, the step heights in the central zone can be modified as well. For example, Table 4, below, illustrates alternative embodiments having different step heights in the central zone.

TABLE 4

Alternative examples of diffractive lens profiles with varying central zones

| Zone | # of Echelettes | Phase Delay (λ) | Step Height (μM) | Position (mm) |
|---|---|---|---|---|
| Central 1* | 1 | 2.51 | 10.3 | 0.84 |
| Central 3 | 1 | 3.2 | 13.13 | 0.84 |

*Note that Central 1 is the same central zone provided above in TABLE 1 and 3.

The central zone is working between the 2nd and 3rd diffractive order for the example Central 1. The central zone is working between the 3rd and 4th diffractive order for the example Central 3. The same peripheral zone 3 as described in the previous example can be combined with other central zones. Within the same peripheral zone, all echelettes have the same step height. The light distributions resulting from the above-referenced combinations of profiles are shown below in Table 5 for the far visual range (i.e. first diffractive order) as well as for two different visual ranges. Visual Range 1 contains the light distribution for the first, second and third diffractive order, while Visual Range 2 contains the light distribution for the diffractive orders at Visual Range 1 as well as the fourth diffractive order:

TABLE 5

Light distributions of diffractive lens profiles with varying central zones

| Order | 1 (Far) | Visual Range 1 | Visual Range 2 |
|---|---|---|---|
| Central 1 + Peripheral | 0.44 | 0.89 | 0.91 |
| Central 3 + Peripheral | 0.43 | 0.86 | 0.91 |

Varying the central zone parameters can adjust the amount of light distributed between the intermediate and near range. For combinations that have a central zone working between the third and fourth diffractive order (i.e. combinations with Central 3), there is an additional, non-trivial amount of light (i.e. greater than 10% of incoming light) distributed to an additional diffraction order to further extend the range of vision. The total light efficiency in distance, intermediate and near is 91%, which is greater than the typical light efficiencies of multifocal IOLs.

Figure 5:
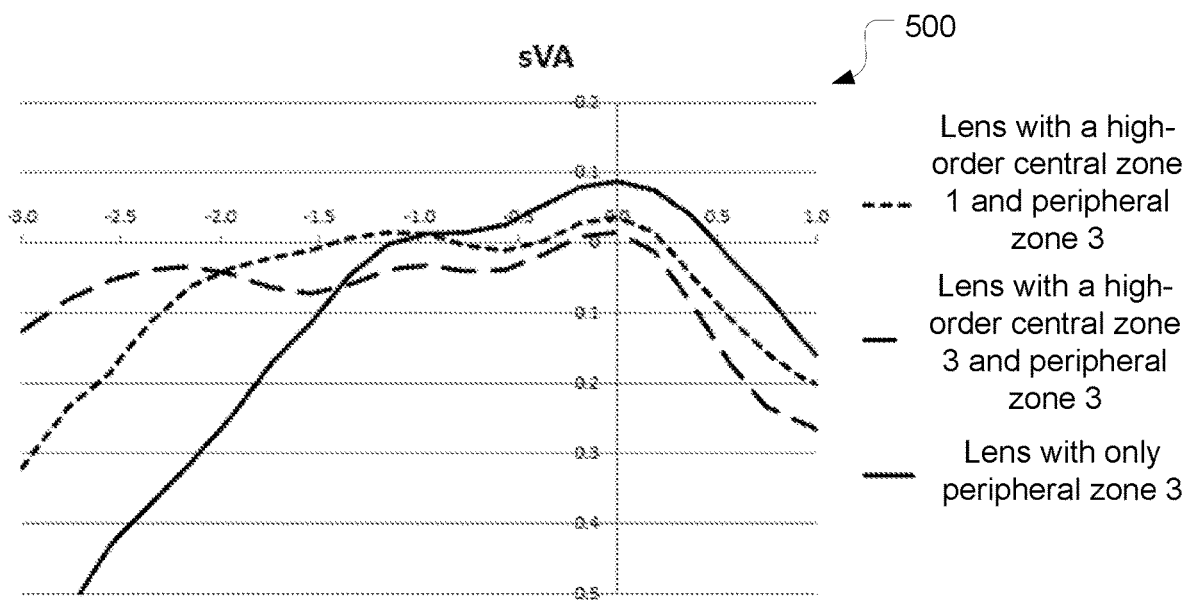
FIG. 5 is a graphical representation showing simulated defocus curves of example lenses having varied central diffractive zones, according to some embodiments of the present invention.

FIG. 5 shows simulated defocus curves 500 showing visual acuity for the example lenses described above with reference to Tables 4-5. In all the cases, the incorporation of the central zone further enlarges the depth of focus with respect to that provided by the peripheral zone alone. Simulated defocus curves show that the near and intermediate visual performance for each lens is affected by the change in step height of the central zone, i.e., increasing the step height further enlarge the depth of focus. The combination with the higher step height creates a continuous range of vision longer than 3 D with at least 0.2 Log MAR visual acuity.

Figure 6:
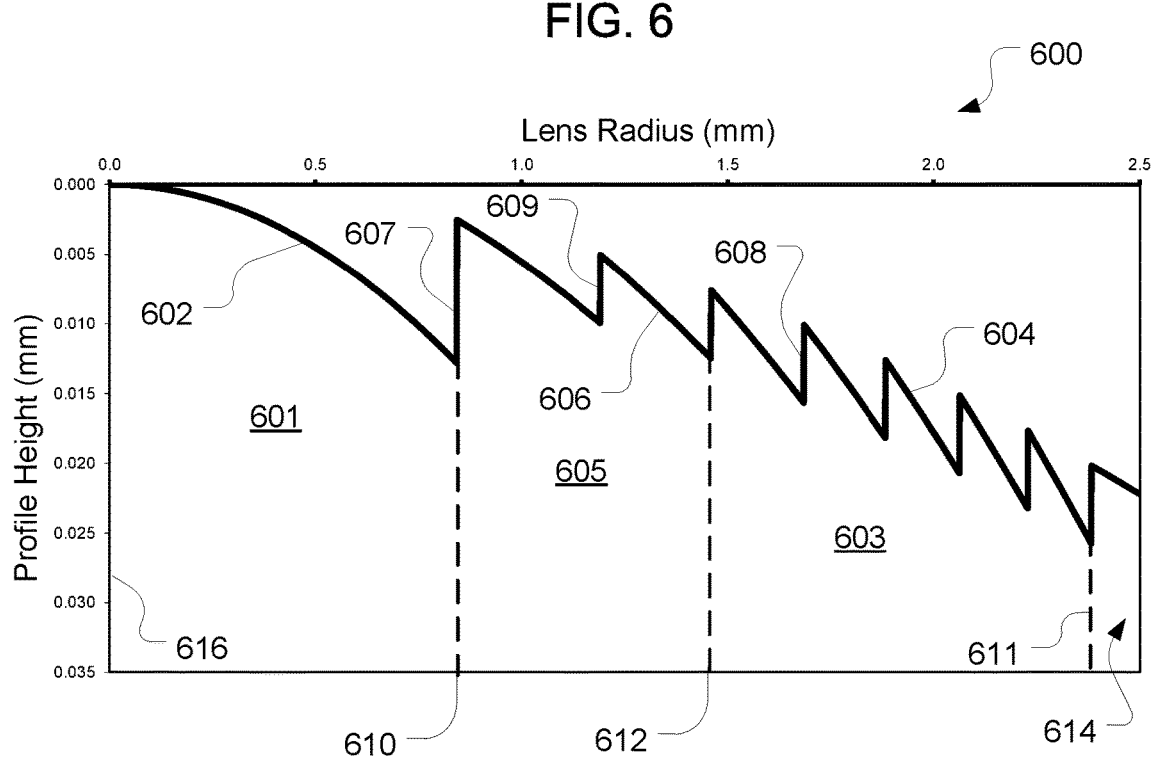
FIG. 6 is a graphical representation of an example diffractive lens profile, showing a central diffractive zone, peripheral diffractive zone, and intermediate diffractive zone, according to some embodiments of the present invention.

FIG. 6 shows graphical representation of an example lens profile 600 having a central echelette 602 in a central diffractive zone 601, multiple intermediate echelettes 606 in an intermediate diffractive zone 605, multiple peripheral echelettes 604 in a peripheral diffractive zone 603 of the lens, and a refractive zone 614 outside of the peripheral diffractive zone 603. The central diffractive zone 601 extends from a lens center 616 to the central zone boundary 610. The intermediate diffractive zone 605 is added between the central and peripheral diffractive zones 601, 603, thus extending from the central zone boundary 610 to the intermediate zone boundary 612. The peripheral zone 603 extends from the intermediate zone boundary 612 to the peripheral zone boundary 611. The intermediate diffractive zone 605 may have one or multiple intermediate echelettes 606. In this example lens profile 600, the intermediate diffractive zone 605 has two echelettes and the peripheral diffractive zone 603 has five. The step heights 609 of the intermediate echelettes 606 are lower than the step heights 608 of the peripheral echelettes 604 in the example shown, however, the step heights of the intermediate echelettes may be higher than in the peripheral diffractive zone in alternative embodiments. The specific lens profile shown is described below in Table 6. Positions are shown in terms of the diffractive zone boundary relative to the lens center. The position of each particular echelette is determined by the position of the first (i.e. 0.84 mm in the example at Table 6) multiplied by the squared root of the echelette number.

TABLE 6

Examples of diffractive lens profiles with an intermediate zone

| Zone | # of Echelettes | Phase Delay (λ) | Step Height (μM) | Position (mm) |
|---|---|---|---|---|
| Central (601) | 1 | 2.51 | 10.3 (607) | 0.84 (610) |
| Intermediate (605) | 2 | 1.20 | 4.9 (609) | 1.46 (612) |
| Peripheral (603) | 5 | 1.366 | 5.6 (608) | 2.38 (611) |
| Refractive (614) | 0 | 0 | 0 | >2.38 (614) |

Figure 7:
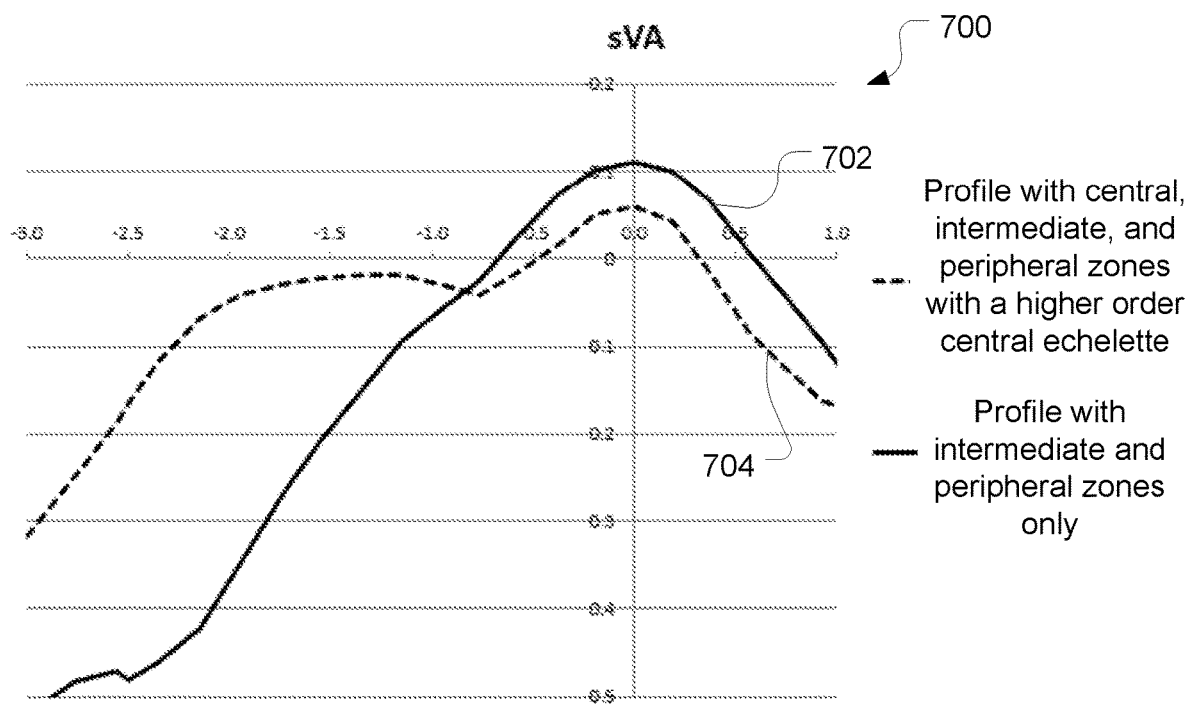
FIG. 7 is a graphical representation of simulated defocus curves of example lenses having a central diffractive zone, intermediate diffractive zone, and peripheral diffractive zone, similar to the lens of FIG. 6, with comparison to a lens having only peripheral and intermediate diffractive zones, according to some embodiments of the present invention.

FIG. 7 shows simulated defocus curves 700 for the example lenses shown in FIG. 6 and described in Table 6 as compared to that of a profile without the higher order echelette (i.e. with the same intermediate, peripheral and refractive zones). In that profile, the central echelette has the same step height as the intermediate zone. FIG. 7 shows that the incorporation of the central echelette increases the depth of focus provided by the combination of the intermediate and peripheral diffractive profiles by approximately 1 D, for a cut-off visual acuity of 0.2 Log MAR.

Table 7 shows the light distribution calculated for 3 mm and 5 mm pupil for the diffractive profile at Table 6 and for a sibling diffractive profile that does not incorporate the intermediate zone. Therefore, this sibling profile has also 8 echelettes, being the central the same as in Table 6 and the remaining 7 echelettes according to the description for the peripheral zone provided in Table 6. Light distribution is shown at Table 7 for distance as well as for the range of vision provided by the lens (i.e. distance and extended depth of focus). Table 7 shows that, for a 3 mm pupil, there is a 58% of light directed to distance when the intermediate zone is included in the diffractive profile, while there is a 44% of light for far without this zone. For a 5 mm pupil the light distribution at distance are 61% and 51% for the profiles with and without the intermediate zone. Therefore, the incorporation of the intermediate zone 605 (FIG. 6) can provide an improvement in the light distribution at distance for both photopic (i.e. 3 mm pupil) and mesopic conditions (i.e. 5 mm pupil) as compared to the case when only the central and peripheral zones are included in the diffractive profile. Furthermore, the amount of light directed to distance is less affected by changes in pupil size when the intermediate zone is included in the combination. While the light directed to distance changes by 5% for the combination with the intermediate diffractive zone, there is a change of 27% in light distribution for distance when only the central and peripheral zones are combined.

TABLE 7

Light distributions of diffractive lens profiles with varying zone configurations

| Order | | 1 (far focus) | Visual Range |
|---|---|---|---|
| Central + Intermediate + Peripheral | 3 mm pupil | 0.58 | 0.92 |
| | 5 mm pupil | 0.61 | 0.90 |
| Central 1 + Peripheral (no intermediate) | 3 mm pupil | 0.44 | 0.89 |
| | 5 mm pupil | 0.56 | 0.89 |

According to various embodiments, the phase delay in the central echelette can be larger than 2λ and smaller than 4λ. In specific embodiments, phase delay can range from about 2.3λ up to 3.5λ, or from 2.45λ to 3.2λ, or from 2.5λ to 2.95λ. The number of echelettes can be determined based on the desired geometry of each echelette and the available radius. In some specific embodiments, the number of echelettes may vary from as few as 8 to up to 32. The first echelette may be positioned with an echelette boundary between 0.5 and 0.9 mm from a center of the lens, with a remainder of the echelettes placed according the position of the first echelette multiplied by the square root of the echelette number. In some embodiments, the phase delay of the peripheral echelettes can range from 1λ and can be smaller than 2λ. In specific embodiments, phase delay can range from about 1λ up to 1.5λ, or from 1.2λ to 1.5λ, or from 1.336λ to 1.5λ. In some embodiments, the phase delay of the echelettes in the intermediate zone can be smaller than that of the echelettes at the peripheral zone by 0.05λ up to 0.5λ, or by 0.10λ to 0.25λ. In alternative embodiments, the phase delay of the echelettes in the intermediate zone may vary. In alternative embodiments, the phase delay of the echelettes in the intermediate zone may be greater than that of the echelettes in the peripheral zone by 0.05λ up to 0.5λ, or by 0.05λ to 0.15λ.

Exemplary Light Distributions by Diffractive Order

Specific light distributions across the visual range of the extended depth of field can be calculated in part on the basis of the portion of light directed by each diffractive order in each respective diffractive zone. For example, Table 8, below, lists light distributions according to diffractive order for a specific embodiment of a diffractive ERV lens similar to the lens of FIG. 1 and Table 1, i.e. having central and peripheral diffractive zones, where the central diffractive zone operates predominantly in a higher order than the remaining echelettes. As shown, a majority of light that passes through the central diffractive zone is directed according to the second and third diffractive orders, whereas a majority of light that passes through the peripheral zone is directed according to the first and second diffractive orders. Total light distribution for the combined lens profile is also shown, with approximately 60%° of light directed to the first diffractive order that provides the distance visual range, and 19% and 14% are directed to the second and third diffractive orders that create the extended depth of focus. All, first, second and third diffractive orders have a non-negligible light distribution (i.e. greater than 10%) and create an extended range of vision that covers distance, intermediate and near as shown in FIG. 3. The combined diffractive profile directs 92% of light toward the entire range of vision. Therefore, it is more efficient than traditional bifocal diffractive lenses that lose approximately 18% of the light (82% is used for the entire range of vision).

TABLE 8

Light Distribution by Diffractive Order across Central and Peripheral Diffractive Zones for profile described in Table 1

| Order | 0 | 1 distance | 2 EDF | 3 EDF | 4 | Visual Range |
|---|---|---|---|---|---|---|
| Central | 0.01 | 0.03 | 0.43 | 0.43 | 0.03 | 0.89 |
| Peripheral | 0.02 | 0.85 | 0.07 | 0.01 | 0.00 | 0.94 |
| Combined | 0.02 | 0.60 | 0.19 | 0.14 | 0.01 | 0.92 |

Table 9, below, lists light distributions according to diffractive order for a specific embodiment of a diffractive ERV lens similar to the lenses described in Table 3, i.e. having the same central zone and different peripheral diffractive zones, where the central diffractive zone operates predominantly in a higher order than the remaining echelettes. As shown, a majority of light that passes through the central diffractive zone is directed according to the second and third diffractive orders. For the peripheral1 diffractive profile, the majority of light is directed according to the first diffractive order. For the peripheral3 diffractive profile, the majority of light is directed according to the first and second diffractive orders. Total light distributions for the combined lens profiles are also shown. In both cases, there is a non-negligible amount of light directed to the first, second and third diffractive orders. The light distribution for distance is greater for the combination with peripheral 1 than for the combination with peripheral 3. However, the light distribution at the second diffractive order is greater for the combination with the peripheral3 profile. That results in a better intermediate performance for this combination, as shown in FIG. 4. The light distribution at the third diffractive order is quite insensitive to modifications in the peripheral diffractive profile. In both cases, the combined diffractive profile directs at least 89% of light toward the extended range of vision. Therefore, it is more efficient than traditional bifocal diffractive lenses that loss approximately 18% of the light.

TABLE 9

Light Distribution by Diffractive Order across Central and Peripheral Diffractive Zones for profile described in Table 3

| order | 0 | 1 distance | 2 EDF | 3 EDF | 4 | Visual Range |
|---|---|---|---|---|---|---|
| Central | 0.01 | 0.03 | 0.43 | 0.43 | 0.03 | 0.89 |
| Peripheral1 | 0.01 | 0.98 | 0.01 | 0.00 | 0.00 | 0.99 |
| Peripheral3 | 0.04 | 0.62 | 0.23 | 0.03 | 0.01 | 0.89 |
| Central + Peripheral1 | 0.01 | 0.68 | 0.14 | 0.14 | 0.01 | 0.96 |
| Central + Peripheral3 | 0.03 | 0.44 | 0.29 | 0.16 | 0.02 | 0.89 |

Table 10, below, lists light distributions according to diffractive order for a specific embodiment of a diffractive ERV lens similar to the lenses described in Table 4, i.e. having the same peripheral and different peripheral central zones, where the central diffractive zones operates predominantly in a higher order than the remaining echelettes. As shown for central 1, a majority of light that passes through any of the central diffractive zone is directed according to the second and third diffractive orders. However, for central 3, a majority of light that passes through any of the central diffractive zone is directed according to the third and fourth diffractive orders. For the peripheral diffractive profile, the majority of light is directed according to the first and second diffractive orders. Total light distributions for the combined lens profiles are also shown. For the combination with central 1, there is a non-negligible amount of light directed to the first, second and third diffractive orders. For the combination with central 3, there is a non-negligible amount of light directed to the first, second, third and fourth diffractive orders. That results in longer depth of focus for this combination, as shown in FIG. 5. In both cases, the combined diffractive profile directs at least 89% of light toward the extended range of vision. Therefore, it is more efficient than traditional bifocal diffractive lenses that loss approximately 18% of the light.

TABLE 10

Light Distribution by Diffractive Order across Central and Peripheral Diffractive Zones for profile described in Table 4

| order | 0 | 1 distance | 2 EDF | 3 EDF | 4 EDF | Visual Range |
|---|---|---|---|---|---|---|
| Central 1 | 0.01 | 0.03 | 0.43 | 0.43 | 0.03 | 0.89 |
| Central 3 | 0.00 | 0.01 | 0.03 | 0.76 | 0.15 | 0.95 |
| Peripheral | 0.04 | 0.62 | 0.23 | 0.03 | 0.01 | 0.89 |
| Central1 + Peripheral | 0.03 | 0.44 | 0.29 | 0.16 | 0.02 | 0.89 |
| Central3 + Peripheral | 0.03 | 0.43 | 0.17 | 0.26 | 0.06 | 0.91 |

Table 11, below, lists light distributions according to diffractive order for a specific embodiment of a diffractive ERV lens similar to the lens of FIG. 7 and Table 6, i.e. having central, intermediate, and peripheral diffractive zones, where the central diffractive zone operates predominantly in a higher order than the remaining zones. As shown, a majority of light that passes through the central diffractive zone is directed according to the second and third diffractive orders, whereas a majority of light that passes through the intermediate and peripheral zones is directed according to the first and second diffractive orders. Total light distribution for the combined lens profile is also shown, with approximately 58% of light directed to the first diffractive order, which provides the distance visual range, and 19% and 15% are directed to the second and third diffractive orders, which create the extended depth of focus. All, first, second and third diffractive orders have a non-negligible light distribution (i.e. greater than 10%) and create an extended range of vision that covers distance, intermediate and near as shown in FIG. 7. The combined diffractive profile directs 92% of light toward the extended range of vision. Therefore, it is more efficient than traditional bifocal diffractive lenses that loss approximately 18% of the light.

TABLE 11

Light Distribution by Diffractive Order across Central, Intermediate, and Peripheral Diffractive Zones for profile described in Table 6

| Order | 0 | 1 distance | 2 EDF | 3 EDF | 4 | Visual range |
|---|---|---|---|---|---|---|
| Central | 0.01 | 0.03 | 0.43 | 0.43 | 0.03 | 0.89 |
| Intermediate | 0.02 | 0.85 | 0.07 | 0.01 | 0.00 | 0.94 |
| Peripheral | 0.04 | 0.62 | 0.23 | 0.03 | 0.01 | 0.89 |
| Combined | 0.02 | 0.58 | 0.19 | 0.15 | 0.01 | 0.92 |

According to various embodiments, between 43% and 68% of light may be directed to the $1^{st}$ diffractive order, which provides the distance visual range, between 14% and 29%, may be directed to the second diffractive order and between 14% and 26% may be directed to the third diffractive order, which creates the extended depth of focus. It is further envisioned that for creating useful vision in the intermediate and/or near distances, a non-negligible amount of light of at least 10% should be directed to the second and third diffractive order. Considering the total light loss being at least 4%, the maximum amount of light in the 1st order in this case would be 75%. In order to create maximum visual quality in the intermediate and/or near range without detrimental effect on distance vision, a maximum amount of light of 30% may be directed to the second and/or third diffractive order. As a result, the minimum amount for the first diffractive order would be 40%. Thus, the range for the first diffractive order may be between 40% and 75%, and the ranges for the second and third diffractive orders may be between 10% and 30%.

Figure 8:
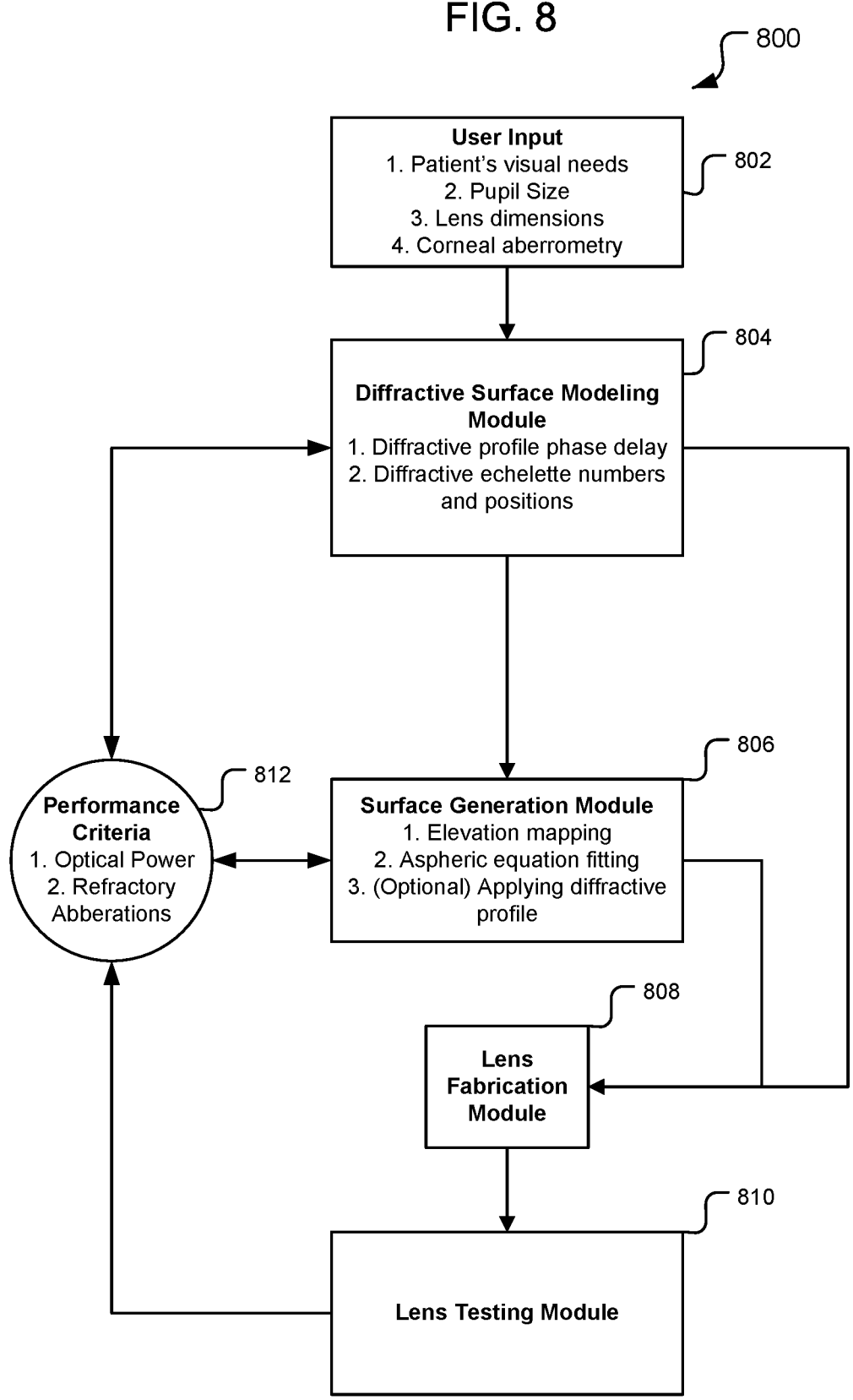
FIG. 8 is a simplified block diagram illustrating a system for generating a diffractive ERV lens surface, in accordance with embodiments.

Systems and Methods for Determining the Diffractive Power Profile:

FIG. 8 is a simplified block diagram illustrating a system 800 for generating a diffractive profile having at least a central higher order echelette and a peripheral zone, in accordance with embodiments. The system 800 may, in some cases, be used to include an intermediate zone. The system 800 may also be used to produce IOLs conforming to the embodiments.

The system 800 includes a user input module 802 configured to receive user input defining aspects of an intraocular lens. Inputs to design an intraocular lens may include a patient's visual needs, corneal aberrations (or corneal topography, from which corneal aberrations can be retrieved), a pupil size performance, and lens dimensions, among other attributes. A simulated optical or visual performance can be calculated from patient's visual needs that represent the desired visual performance of the patient after the surgery. In some cases, a desired optical performance may relate to a patient's lifestyle, e.g., whether the patient prefers to participate in activities requiring predominantly distance vision, intermediate vision, or near vision without additional visual correction. The power profile prescription can be calculated from the simulated performance including, for example, a preferred optical power or optical power profile for correcting far vision and expected depth of focus. The corneal aberrations (or corneal wave front aberrations) can include the higher order rotationally symmetrical aberrations of the cornea as a function of the pupil size. A pupil size performance can include a pupil diameter of a patient under different lighting conditions. These parameters can also be related to patient's life style or profession, so that the design incorporates patient's visual needs as a function of the pupil size. In some cases, parameters such as lens asphericity can be determined based on a function of the wave front aberrations and visual needs of the patient. Lens dimensions can include a preferred radius of the total lens, and may further include preferred thickness, or a preferred curvature of one or the other of the anterior surface and posterior surface of the lens, as well as the optional incorporation of toricity in any of the IOL surfaces.

A diffractive profile modeling module 804 can receive information about the desired lens from the user input module 802, and can determine aspects of the diffractive profile. For example, the diffractive profile modeling module 804 can determine the position and heights of the echelette of the central zone. It can also determine the position, number and height of the echelettes in peripheral zones required to fulfill the performance determined from patient's visual needs. The module can determine the need of including an intermediate zone, as well as the structural characteristics of the zone (number and heights of the echelettes). The base curvature of the profile can be related to the biometry of the patient. The asphericity can also be related to that of the patient's cornea, so that it either compensates patient's corneal spherical aberration or induces a certain amount of spherical aberration to help improving intermediate and near performance in mesopic conditions.

The diffractive profile modeling module 804 can be configured to generate performance criteria 812, e.g. via modeling optical properties in a virtual environment. Performance criteria can include the match of the expected performance derived from patient's visual needs to that of the actual diffractive profile that results from 804. In some cases, the diffractive profile modeling module 804 can provide an intraocular lens surface to an intraocular lens fabrication module 808 for facilitating the production of a physical lens, which can be tested via an intraocular lens testing module 810 for empirically determining the performance criteria 812, so as to identify optical aberrations and imperfections not readily discerned via virtual modeling, and to permit iteration.

Figure 9:
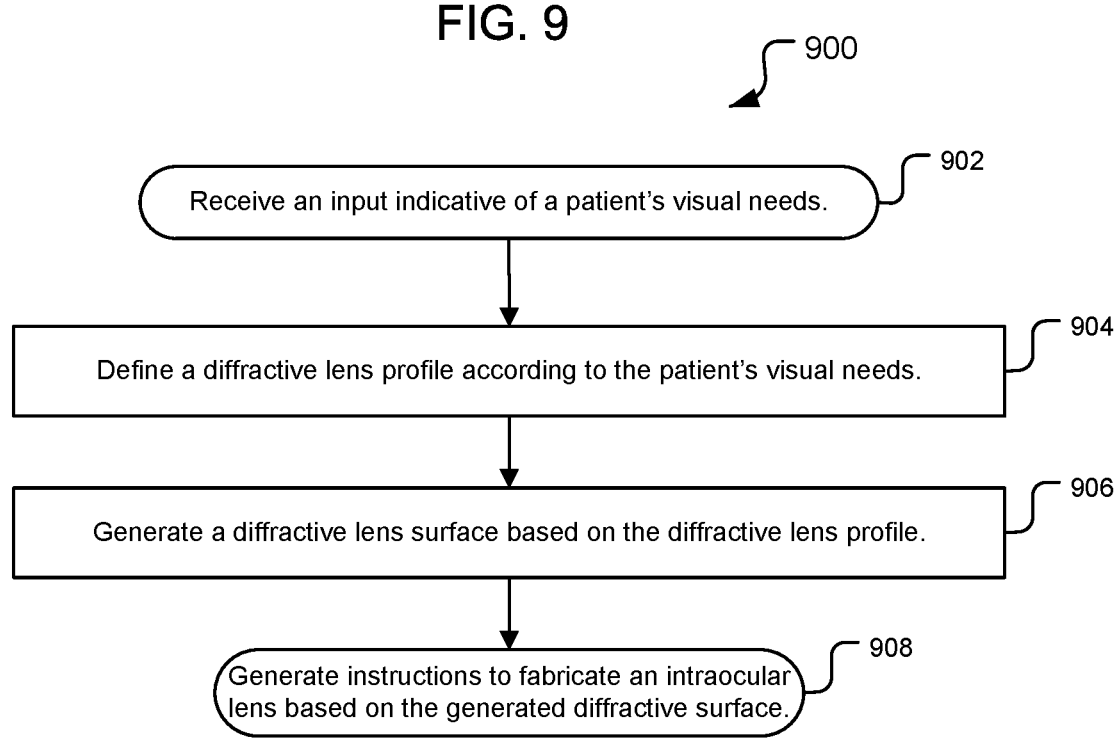
FIG. 9 illustrates an example process for generating a diffractive ERV lens surface.

FIG. 9 is an example process 900 for generating a refractive ERV lens surface, in accordance with embodiments. The process 900 may be implemented in conjunction with, for example, the system 800 shown in FIG. 8. Some or all of the process 900 (or any other processes described herein, or variations, and/or combinations thereof) may be performed under the control of one or more computer systems configured with executable instructions and may be implemented as code (e.g., executable instructions, one or more computer programs, or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

The process 900 includes receiving an input indicative of a patient's visual needs (act 902). The input can include, e.g., a desired optical power profile for correcting impaired distance vision, a desired optical power profile for correcting impaired intermediate vision, a desired optical power profile for accommodating near vision, and any suitable combination of the above. Next, a diffractive ERV lens profile can be defined according to the visual needs determined above (act 904). In some cases, the diffractive profile may be defined for providing an extended depth of focus by, e.g., defining a central diffractive zone including one more echelettes configured to operate primarily in the second and/or third and/or fourth diffractive orders, where the central diffractive zone is operable to direct incident light to a range of distances to further enlarge the depth of focus of the diffractive profile. The diffractive profile may be further defined to include a peripheral diffractive zone configured to operate primarily in a first and/or second diffractive order, or a lower diffractive order than the central diffractive zone, that is operable to direct light to a range of distances corresponding to the intermediate and/or far visual range. A diffractive lens surface can then be generated based on the diffractive profile (act 906). The system can then generate instructions to fabricate an intraocular lens based on the generated diffractive lens surface (act 908).

Figure 10:
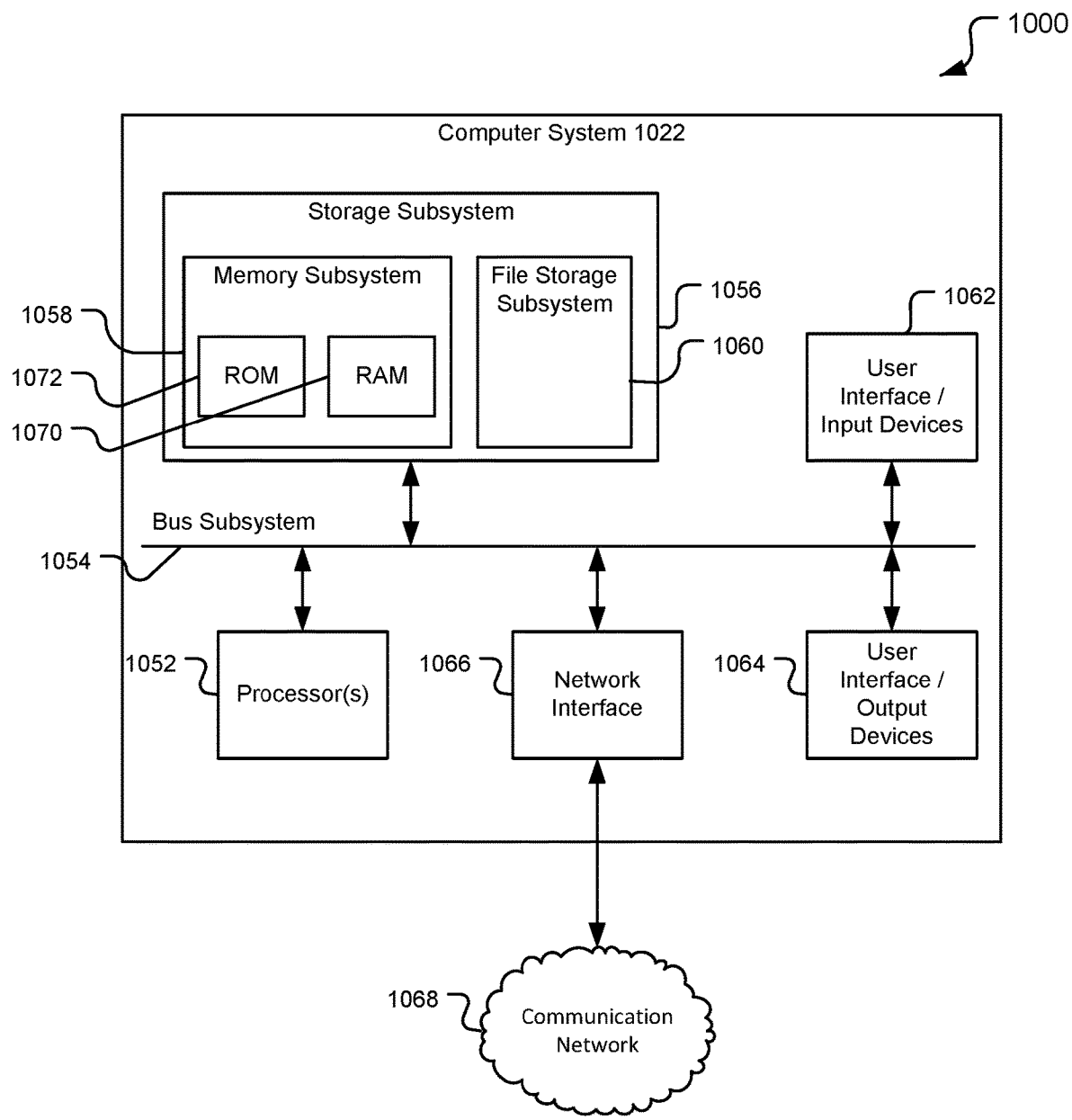
FIG. 10 illustrates an example computing environment for facilitating the systems and processes of FIGS. 8 and 9.

FIG. 10 is a simplified block diagram of an exemplary computing environment 1000 that may be used by systems for generating the continuous progressive lens surfaces of the present disclosure. Computer system 1000 typically includes at least one processor 1052 which may communicate with a number of peripheral devices via a bus subsystem 1054. These peripheral devices may include a storage subsystem 1056 comprising a memory subsystem 1058 and a file storage subsystem 1060, user interface input devices 1062, user interface output devices 1064, and a network interface subsystem 1066. Network interface subsystem 1066 provides an interface to outside networks 1068 and/or other devices, such as the lens fabrication module 808 or lens testing module 810 of FIG. 8. In some cases, some portion of the above-referenced subsystems may be available in a diagnostics device capable of measuring the biometric inputs required for calculating attributes such as base power.

User interface input devices 1062 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. The input devices 1062 may also include one or more biometric input devices capable of measuring a patient's biometric inputs required to generate the diffractive lens surface. For example, input devices 1062 can include a biometer capable of measuring axial length, corneal power, corneal aberrations, preoperative anterior chamber depth, lens thickness, and/or pupil size for a patient under different lighting conditions. These variables are nonlimiting and are mentioned herein by way of example. User input devices 1062 will often be used to download a computer executable code from a tangible storage media embodying any of the methods of the present invention. In general, use of the term "input device" is intended to include a variety of conventional and proprietary devices and ways to input information into computer system 1022.

User interface output devices 1064 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 1022 to a user.

Storage subsystem 1056 can store the basic programming and data constructs that provide the functionality of the various embodiments of the present invention. For example, a database and modules implementing the functionality of the methods of the present invention, as described herein, may be stored in storage subsystem 1056. These software modules are generally executed by processor 1052. In a distributed environment, the software modules may be stored on a plurality of computer systems and executed by processors of the plurality of computer systems. Storage subsystem 1056 typically comprises memory subsystem 1058 and file storage subsystem 1060. Memory subsystem 1058 typically includes a number of memories including a main random access memory (RAM) 1070 for storage of instructions and data during program execution.

Various computational methods discussed above, e.g. with respect to generating a diffractive lens surface, may be performed in conjunction with or using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

The following definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of skill in the art, such as the Oxford Dictionary of Biochemistry and Molecular Biology (Ed. Anthony Smith, Oxford University Press, Oxford, 2004).

As used herein and unless otherwise indicated, the terms "a" and "an" are taken to mean "one", "at least one" or "one or more". Unless otherwise required by context, singular terms used herein shall include pluralities and plural terms shall include the singular.

Unless the context clearly requires otherwise, throughout the description and the claims, the words 'comprise', 'comprising', and the like are to be construed in an inclusive sense as opposed to an exclusive or exhaustive sense, that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

All references, including patent filings (including patents, patent applications, and patent publications), scientific journals, books, treatises, technical references, and other publications and materials discussed in this application, are incorporated herein by reference in their entirety for all purposes.

Aspects of the disclosure can be modified, if necessary, to employ the systems, functions, and concepts of the above references and application to provide yet further embodiments of the disclosure. These and other changes can be made to the disclosure in light of the detailed description.

Specific elements of any foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

While the above provides a full and complete disclosure of exemplary embodiments of the present invention, various modifications, alternate constructions and equivalents may be employed as desired. Consequently, although the embodiments have been described in some detail, by way of example and for clarity of understanding, a variety of modifications, changes, and adaptations will be obvious to those of skill in the art. Accordingly, the above description and illustrations should not be construed as limiting the invention, which can be defined by the appended claims.

What is claimed is:

1. An ophthalmic lens, comprising:
   a first surface and a second surface disposed about an optical axis, the lens being characterized by an extended depth of focus across a range of optical powers; and
   a diffractive profile imposed on one of the first and second surfaces and configured to cause a distribution of non-negligible amounts of light to the extended depth of focus, the diffractive profile comprising:

a central zone comprising at least one central diffractive echelette having a first phase delay;

an intermediate zone comprising at least one intermediate echelette having a second phase delay; and a peripheral zone comprising one or more peripheral diffractive echelettes having a third phase delay;

wherein the central zone is configured to operate in a higher diffractive order than the peripheral zone;

wherein the first, second and third phase delay are different and the third phase delay is less than the first phase delay; and wherein the combination of the central, intermediate and peripheral zones provides a longer depth of focus than a diffractive profile defined just by the peripheral zone, and wherein a step height of a central diffractive echelette of the at least one central diffractive echelette adjacent to the intermediate zone is larger than a step height of an intermediate echelette of the at least one intermediate echelette adjacent to the central zone.

2. The ophthalmic lens of claim 1, wherein the peripheral zone is configured to operate in a first diffractive order by directing light toward a far focal length for distance vision.

3. The ophthalmic lens of claim 1, wherein the peripheral zone is configured to operate in a first diffractive order and a second diffractive order by directing light toward a far focal length for distance vision and to an intermediate focal length for intermediate vision.

4. The ophthalmic lens of claim 1, wherein the central zone is configured to operate in a second diffractive order and a third diffractive order by directing light toward an intermediate focal length for intermediate vision and to a short focal length for near vision.

5. The ophthalmic lens of claim 4, wherein at least the second and third diffractive orders create an extended range of vision.

6. The ophthalmic lens of claim 1, wherein the peripheral zone directs light toward a far focal length.

7. The lens of claim 1, wherein the at least one central diffractive echelette in the central zone has a phase delay of more than $2.0\lambda$, and wherein the one or more peripheral diffractive echelettes have a phase delay of less than $2.0\lambda$.

8. The lens of claim 1, wherein a total number of echelettes defining the central, intermediate and peripheral optical zones is from 8 to 32 echelettes.

9. The lens of claim 1, wherein the central optical zone has a phase shift from $2\lambda$ to $4\lambda$ and wherein the peripheral optical zone has a phase shift from $1\lambda$ to $2\lambda$.

10. The lens of claim 1, wherein the central optical zone comprises 1 to 2 central echelettes, and wherein the peripheral optical zone comprises 5 to 7 peripheral echelettes.

11. The ophthalmic lens of claim 1, wherein the intermediate zone is configured to operate in a first diffractive order by directing light toward a far focal length for distance vision.

12. The ophthalmic lens of claim 1, wherein the phase delay of the at least one echelette in the intermediate zone is smaller than that of the one or more peripheral diffractive echelettes by $0.05\lambda$, up to $0.5\lambda$.

13. The ophthalmic lens of claim 1, wherein there is a non-negligible light distribution in a first diffractive order, a second diffractive order and a third diffractive order of the diffractive profile, wherein the first diffractive order directs light toward a far focal length for distance vision, the second diffractive order directs light toward an intermediate focal length for intermediate vision, and the third diffractive order directs light to a short focal length for near vision.

14. The lens of claim 1, wherein the lens is an intraocular implant.

15. The lens of claim 1, further comprising two principal meridians with different base powers.

16. The lens of claim 1, wherein the central zone comprises 1 echelette.

17. An ophthalmic lens, comprising:

a first surface and a second surface disposed about an optical axis, the lens being characterized by an extended depth of focus across a range of optical powers; and a diffractive profile imposed on one of the first and second surfaces and configured to cause a distribution of non-negligible amounts of light to the extended depth of focus, the diffractive profile comprising:

a central zone comprising at least one central diffractive echelette having a first phase delay;

an intermediate zone comprising at least one intermediate echelette having a second phase delay; and a peripheral zone comprising one or more peripheral diffractive echelettes having a third phase delay;

wherein the central zone is configured to operate in a higher diffractive order than the peripheral zone;

wherein the first, second and third phase delay are different and the third phase delay is less than the first phase delay;

wherein the combination of the central, intermediate and peripheral zones provides a longer depth of focus than a diffractive profile defined just by the peripheral zone; and wherein a light distribution for a distance focus ranges between 75% and 40% of light incident on the lens.

18. The ophthalmic lens of claim 17, wherein a light directed to a distance focus of the extended depth of focus ranges from between 58% and 61% of incident light on the diffractive profile.

19. The ophthalmic lens of claim 17, wherein light directed to a full range of vision provided by the lens ranges from 90% to 92% of light incident on the lens.

20. The ophthalmic lens of claim 17, wherein at least 90% of incident light on the lens is directed to a full range of vision provided by diffractive profile.

21. An ophthalmic lens, comprising:

a first surface and a second surface disposed about an optical axis, the lens being characterized by an extended depth of focus across a range of optical powers; and a diffractive profile imposed on one of the first and second surfaces and configured to cause a distribution of non-negligible amounts of light to the extended depth of focus provided by the lens wherein the diffractive profile comprises a central diffractive zone that works in a higher diffractive order than a remainder of the diffractive profile, wherein the central diffractive zone has a phase delay from $2.3\lambda$ to $3.5\lambda$.

22. The lens of claim 21, wherein the central diffractive zone has a phase delay from $2.45\lambda$ to $3.2\lambda$.

23. The lens of claim 21, wherein the central diffractive zone has a phase delay from $2.5\lambda$ to $2.95\lambda$.

24. The lens of claim 21, wherein the remainder of the diffractive profile has a phase delay of between $1\lambda$ and $1.5\lambda$.

25. The lens of claim 21, wherein the remainder of the diffractive profile has a phase delay of between $1.2\lambda$ and $1.5\lambda$.

26. The lens of claim 21, wherein the remainder of the diffractive profile has a phase delay of between 1.2 and 1.336λ.

27. The lens of claim 21, wherein the diffractive profile is operable to mitigate ocular chromatic aberration imparted by the lens.

28. The lens of claim 21, wherein: the first surface is a posterior surface of the lens and the second surface is an anterior surface of the lens; and the diffractive profile is disposed on the first surface.

29. The lens of claim 21, further comprising a refractive profile disposed on one of the first surface and the second surface, the refractive profile being configured to correct for corneal spherical aberration.

30. The lens of claim 21, further comprising a refractive profile disposed on one of the first surface and the second surface, the refractive profile being configured to correct for corneal astigmatism.

31. The lens of claim 21, wherein the lens is an intraocular implant.

32. The lens of claim 21, wherein the remainder of the diffractive profile comprises echelettes configured to operate in a first diffractive order by directing light toward a far focal length for distance vision and that have phase delays less than 2λ.

33. The lens of claim 21, wherein the central zone comprises 1 echelette.

\* \* \* \* \*